United States Patent
Dobak, III et al.

(10) Patent No.: US 7,998,182 B2
(45) Date of Patent: *Aug. 16, 2011

(54) SELECTIVE ORGAN COOLING APPARATUS

(75) Inventors: John D. Dobak, III, La Jolla, CA (US);
Juan C. Lasheras, La Jolla, CA (US);
Randell L. Werneth, Poway, CA (US)

(73) Assignee: Innercool Therapies, Inc., San Diego, CA (US)

( * ) Notice: Subject to any disclaimer, the term of this patent is extended or adjusted under 35 U.S.C. 154(b) by 1281 days.

This patent is subject to a terminal disclaimer.

(21) Appl. No.: 11/333,986

(22) Filed: Jan. 17, 2006

(65) Prior Publication Data

US 2006/0116734 A1 Jun. 1, 2006

Related U.S. Application Data

(63) Continuation of application No. 10/796,906, filed on Mar. 8, 2004, now Pat. No. 7,066,948, which is a continuation of application No. 10/161,107, filed on May 30, 2002, now Pat. No. 6,702,842, which is a continuation of application No. 09/607,799, filed on Jun. 30, 2000, now Pat. No. 6,464,716, which is a continuation-in-part of application No. 09/570,075, filed on May 12, 2000, now Pat. No. 6,471,717, and a continuation-in-part of application No. 09/215,041, filed on Dec. 16, 1998, now Pat. No. 6,254,626, and a continuation-in-part of application No. 09/103,342, filed on Jun. 23, 1998, now Pat. No. 6,096,068, and a continuation-in-part of application No. 09/052,545, filed on Mar. 31, 1998, now Pat. No. 6,231,595, and a continuation-in-part of application No. 09/047,012, filed on Mar. 24, 1998, now Pat. No. 5,957,963, and a continuation-in-part of application No. 09/012,287, filed on Jan. 23, 1998, now Pat. No. 6,051,019.

(51) Int. Cl.
*A61F 7/00* (2006.01)
(52) U.S. Cl. .................. 607/105; 607/104; 607/106
(58) Field of Classification Search .......... 607/104–107
See application file for complete search history.

(56) References Cited

U.S. PATENT DOCUMENTS

| 1,011,606 A | 12/1911 | Fulton |
| 2,077,453 A | 4/1937 | Albright |

(Continued)

FOREIGN PATENT DOCUMENTS

AU 730835 B2 3/2001

(Continued)

OTHER PUBLICATIONS

Alfonsi, P., D. I. Sessler, B. Du Manoir, J-C. Levron, J-P. Le Moing, M. Chauvin, "The Effects of Meperidine and Sufentanil on the Shivering Threshold in Postoperative Patients," *Anesthesiology*, Jul. 1998, 89(1):43-48.

(Continued)

*Primary Examiner* — Roy D Gibson

(57) ABSTRACT

An endovascular heat transfer device which can have a smooth exterior surface, or a surface with ridges and grooves. The device can have a plurality of elongated, articulated segments, with each having such a surface. A flexible joint connects adjacent elongated, articulated segments. The flexible joints can be bellows or flexible tubes. An inner lumen is disposed within the heat transfer segments. The inner lumen is capable of transporting a pressurized working fluid to a distal end of the heat transfer element.

10 Claims, 8 Drawing Sheets

U.S. PATENT DOCUMENTS

| | | |
|---|---|---|
| 2,148,541 A | 2/1939 | Dierker |
| 2,308,484 A | 1/1943 | Auzin et al. |
| 2,374,609 A | 4/1945 | McCollum |
| 2,466,042 A | 4/1949 | Reich |
| 2,615,686 A | 10/1952 | Davidson |
| 2,672,032 A | 3/1954 | Towse |
| 2,913,009 A | 11/1959 | Kuthe |
| 3,087,493 A | 4/1963 | Schossow |
| 3,125,096 A | 3/1964 | Antiles et al. |
| 3,298,371 A | 1/1967 | Lee |
| 3,425,419 A | 2/1969 | Dato |
| 3,460,538 A | 8/1969 | Armstrong |
| 3,504,674 A | 4/1970 | Swenson et al. |
| 3,604,419 A | 9/1971 | Diskin et al. |
| 3,612,175 A | 10/1971 | Ford et al. |
| 3,768,484 A | 10/1973 | Gawura |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,072,146 A | 2/1978 | Howes |
| 4,111,209 A | 9/1978 | Wolvek et al. |
| 4,153,048 A | 5/1979 | Magrini |
| 4,160,455 A | 7/1979 | Law |
| 4,190,033 A | 2/1980 | Foti |
| 4,216,767 A | 8/1980 | Aoshiro |
| 4,231,425 A | 11/1980 | Engstrom |
| 4,241,729 A | 12/1980 | Aoshiro |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,427,009 A | 1/1984 | Wells et al. |
| 4,445,500 A | 5/1984 | Osterholm |
| 4,464,172 A | 8/1984 | Lichtenstein |
| 4,483,341 A | 11/1984 | Witteles |
| 4,484,586 A | 11/1984 | McMickle et al. |
| 4,497,890 A | 2/1985 | Helbert |
| 4,502,286 A | 3/1985 | Okada et al. |
| RE31,873 E | 4/1985 | Howes |
| 4,569,355 A | 2/1986 | Bitterly |
| 4,581,017 A | 4/1986 | Sahota |
| 4,602,642 A | 7/1986 | O'Hara et al. |
| 4,655,746 A | 4/1987 | Daniels et al. |
| 4,672,962 A | 6/1987 | Hershenson |
| 4,731,072 A | 3/1988 | Aid |
| 4,739,492 A | 4/1988 | Cochran |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,799 A | 11/1988 | Herbert, Jr. et al. |
| 4,796,640 A | 1/1989 | Webler |
| 4,817,624 A | 4/1989 | Newbower |
| 4,819,655 A | 4/1989 | Webler |
| 4,820,349 A | 4/1989 | Saab |
| 4,860,744 A | 8/1989 | Johnson et al. |
| 4,863,442 A | 9/1989 | DeMello et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowley et al. |
| 4,964,409 A | 10/1990 | Tremulis |
| 4,973,493 A | 11/1990 | Guire |
| 4,979,959 A | 12/1990 | Guire |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishiwara et al. |
| 5,106,368 A | 4/1992 | Uldall et al. |
| 5,108,390 A | 4/1992 | Potocky et al. |
| RE33,911 E | 5/1992 | Samson et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,236,908 A | 8/1993 | Gruber et al. |
| 5,246,421 A | 9/1993 | Saab |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,306,261 A | 4/1994 | Alliger et al. |
| 5,310,440 A | 5/1994 | Zingher |
| 5,322,514 A | 6/1994 | Steube et al. |
| 5,322,515 A | 6/1994 | Karas et al. |
| 5,322,518 A | 6/1994 | Schneider et al. |
| 5,326,165 A | 7/1994 | Walthall et al. |
| 5,326,166 A | 7/1994 | Walthall et al. |
| 5,330,435 A | 7/1994 | Vaillancourt |
| 5,330,519 A | 7/1994 | Mason et al. |
| 5,334,193 A | 8/1994 | Nardella |
| 5,342,301 A | 8/1994 | Saab |
| 5,344,436 A | 9/1994 | Fontenot et al. |
| 5,344,740 A | 9/1994 | Iwasawa et al. |
| 5,364,364 A | 11/1994 | Kasvikis et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Alliger et al. |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,496,311 A | 3/1996 | Abele et al. |
| 5,499,973 A | 3/1996 | Saab |
| 5,520,682 A | 5/1996 | Baust et al. |
| 5,531,776 A | 7/1996 | Ward et al. |
| 5,536,247 A | 7/1996 | Thornton |
| 5,545,708 A | 8/1996 | Onwunaka et al. |
| 5,549,559 A | 8/1996 | Eshel |
| 5,554,119 A | 9/1996 | Harrison et al. |
| 5,558,644 A | 9/1996 | Boyd et al. |
| 5,569,195 A | 10/1996 | Saab |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,617,854 A | 4/1997 | Munsif |
| 5,620,480 A | 4/1997 | Rudie |
| 5,622,182 A | 4/1997 | Jaffe |

| | | |
|---|---|---|
| 5,624,342 A | 4/1997 | Younger |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,676,693 A | 10/1997 | LaFontaine |
| 5,709,654 A | 1/1998 | Klatz et al. |
| 5,713,848 A | 2/1998 | Dubrul et al. |
| 5,713,941 A | 2/1998 | Robins et al. |
| 5,716,386 A | 2/1998 | Ward et al. |
| 5,733,318 A | 3/1998 | Augustine |
| 5,733,319 A | 3/1998 | Neilson et al. |
| 5,735,809 A | 4/1998 | Gorsuch |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,486 A | 9/1998 | Thome et al. |
| 5,800,488 A | 9/1998 | Crockett |
| 5,800,493 A | 9/1998 | Stevens et al. |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,833,673 A | 11/1998 | Ockuly et al. |
| 5,834,465 A | 11/1998 | Olney |
| 5,837,003 A | 11/1998 | Ginsburg |
| 5,861,021 A | 1/1999 | Thome et al. |
| 5,868,735 A | 2/1999 | Lafontaine |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,891,094 A | 4/1999 | Masterson et al. |
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,910,104 A | 6/1999 | Dobak, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,917 A | 9/1999 | Doiron et al. |
| 5,957,963 A | 9/1999 | Dobak, III |
| 5,964,751 A | 10/1999 | Amplatz et al. |
| 5,967,976 A | 10/1999 | Larsen et al. |
| 5,968,009 A | 10/1999 | Simám |
| 5,971,979 A | 10/1999 | Joye et al. |
| 5,989,238 A | 11/1999 | Ginsburg |
| 6,007,692 A | 12/1999 | Herbert et al. |
| 6,011,995 A | 1/2000 | Guglielmi et al. |
| 6,019,783 A | 2/2000 | Phillips et al. |
| 6,022,336 A | 2/2000 | Zadno-Azizi et al. |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,063,101 A | 5/2000 | Jacobsen et al. |
| 6,096,068 A | 8/2000 | Dobak, III |
| 6,110,168 A | 8/2000 | Ginsburg |
| 6,113,626 A | 9/2000 | Clifton et al. |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,182,666 B1 | 2/2001 | Dobak, III |
| 6,194,899 B1 | 2/2001 | Ishihara et al. |
| 6,206,004 B1 | 3/2001 | Schmidt et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,277,143 B1 | 8/2001 | Klatz et al. |
| 6,287,326 B1 | 9/2001 | Pecor |
| 6,290,697 B1 | 9/2001 | Tu et al. |
| 6,290,717 B1 | 9/2001 | Philips |
| 6,295,990 B1 | 10/2001 | Lewis et al. |
| 6,299,599 B1 | 10/2001 | Pham et al. |
| 6,306,161 B1 | 10/2001 | Ginsburg |
| 6,312,452 B1 | 11/2001 | Dobak, III et al. |
| 6,315,754 B1 | 11/2001 | Daoud et al. |
| 6,319,248 B1 | 11/2001 | Nahon |
| 6,325,818 B1 | 12/2001 | Werneth |
| 6,336,911 B1 | 1/2002 | Westerbeck |
| 6,338,727 B1 | 1/2002 | Noda et al. |
| 6,355,029 B1 | 3/2002 | Joye et al. |
| 6,364,899 B1 | 4/2002 | Dobak, III |
| 6,368,304 B1 | 4/2002 | Aliberto et al. |
| 6,379,378 B1 | 4/2002 | Werneth et al. |
| 6,383,210 B1 | 5/2002 | Magers et al. |
| 6,393,320 B2 | 5/2002 | Lasersohn et al. |
| 6,405,080 B1 | 6/2002 | Lasersohn et al. |
| 6,409,747 B1 | 6/2002 | Gobin et al. |
| 6,416,533 B1 | 7/2002 | Gobin et al. |
| 6,419,643 B1 | 7/2002 | Shimada et al. |
| 6,432,102 B2 | 8/2002 | Joye et al. |
| 6,432,124 B1 | 8/2002 | Worthen et al. |
| 6,436,071 B1 | 8/2002 | Schwartz |
| 6,436,130 B1 | 8/2002 | Philips et al. |
| 6,436,131 B1 | 8/2002 | Ginsburg |
| 6,520,933 B1 | 2/2003 | Evans et al. |
| 6,572,638 B1 | 6/2003 | Dae et al. |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 | 6/2001 | Ginsburg et al. |
| 2001/0007951 A1 | 7/2001 | Dobak, III |
| 2001/0008975 A1 | 7/2001 | Dobak, III et al. |
| 2001/0010011 A1 | 7/2001 | Aliberto et al. |
| 2001/0011184 A1 | 8/2001 | Dobak, III et al. |
| 2001/0011185 A1 | 8/2001 | Dobak, III et al. |
| 2001/0014802 A1 | 8/2001 | Tu |
| 2001/0016763 A1 | 8/2001 | Lasheras et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0027333 A1 | 10/2001 | Schwartz |
| 2001/0029394 A1 | 10/2001 | Dobak, III et al. |
| 2001/0031946 A1 | 10/2001 | Walker et al. |
| 2001/0032003 A1 | 10/2001 | Pecor |
| 2001/0032004 A1 | 10/2001 | Werneth |
| 2001/0039440 A1 | 11/2001 | Lasheras et al. |
| 2001/0041923 A1 | 11/2001 | Dobak, III |
| 2001/0044644 A1 | 11/2001 | Keller et al. |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049545 A1 | 12/2001 | Lasersohn et al. |
| 2002/0002394 A1 | 1/2002 | Dobak, III |
| 2002/0004675 A1 | 1/2002 | Lasheras |
| 2002/0007179 A1 | 1/2002 | Dobak, III et al. |
| 2002/0007202 A1 | 1/2002 | Dobak, III et al. |
| 2002/0007203 A1 | 1/2002 | Gilmartin et al. |
| 2002/0016621 A1 | 2/2002 | Werneth et al. |
| 2002/0022823 A1 | 2/2002 | Luo et al. |
| 2002/0026227 A1 | 2/2002 | Philips |
| 2002/0029016 A1 | 3/2002 | Pham et al. |
| 2002/0032430 A1 | 3/2002 | Luo et al. |

| | | | |
|---|---|---|---|
| 2002/0032474 A1 | 3/2002 | Dobak, III et al. | |
| 2002/0040717 A1 | 4/2002 | Dobak, III | |
| 2002/0045852 A1 | 4/2002 | Saab | |
| 2002/0045892 A1 | 4/2002 | Kramer | |
| 2002/0045925 A1 | 4/2002 | Keller et al. | |
| 2002/0049409 A1 | 4/2002 | Noda et al. | |
| 2002/0049410 A1 | 4/2002 | Noda et al. | |
| 2002/0049484 A1 | 4/2002 | Werneth et al. | |
| 2002/0066458 A1 | 6/2002 | Aliberto et al. | |
| 2002/0068964 A1 | 6/2002 | Dobak, III | |
| 2002/0082671 A1 | 6/2002 | Daoud et al. | |
| 2002/0091378 A1 | 7/2002 | Dobak, III et al. | |
| 2002/0091429 A1 | 7/2002 | Dobak, III et al. | |
| 2002/0091430 A1 | 7/2002 | Dobak, III et al. | |
| 2002/0095200 A1 | 7/2002 | Dobak, III et al. | |
| 2002/0095201 A1 | 7/2002 | Worthen et al. | |
| 2002/0099427 A1 | 7/2002 | Dobak, III | |
| 2002/0103519 A1 | 8/2002 | Dobak, III et al. | |
| 2002/0111616 A1 | 8/2002 | Dae et al. | |
| 2002/0111657 A1 | 8/2002 | Dae et al. | |
| 2002/0116039 A1 | 8/2002 | Walker et al. | |
| 2002/0151946 A1 | 10/2002 | Dobak, III | |
| 2003/0014094 A1 | 1/2003 | Hammack et al. | |
| 2003/0060863 A1 | 3/2003 | Dobak, III et al. | |
| 2003/0120210 A1 | 6/2003 | Worthen et al. | |
| 2004/0064171 A1 | 4/2004 | Briscoe et al. | |
| 2004/0087606 A1 | 5/2004 | Voorhees | |
| 2004/0116988 A1 | 6/2004 | Hammack et al. | |

FOREIGN PATENT DOCUMENTS

| | | |
|---|---|---|
| AU | 739996 B2 | 10/2001 |
| AU | 734506 B2 | 11/2001 |
| AU | 743945 B2 | 2/2002 |
| EP | 0655225 A1 | 5/1993 |
| EP | 0 664 990 | 11/1997 |
| EP | 0428505 B2 | 3/2001 |
| EP | 1205167 A2 | 5/2002 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 97/32518 | 9/1997 |
| WO | WO 98/26831 | 6/1998 |
| WO | WO 98/31312 | 7/1998 |
| WO | WO 98/49957 | 11/1998 |
| WO | WO 99/02096 | 1/1999 |
| WO | WO 99/37226 | 7/1999 |
| WO | WO 99/44519 | 9/1999 |
| WO | WO 99/48449 | 9/1999 |
| WO | WO 99/56812 | 11/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 4/2001 |
| WO | WO 01/41708 | 6/2001 |
| WO | WO 01/43661 | 6/2001 |
| WO | WO 01/49236 | 7/2001 |
| WO | WO 01/50987 | 7/2001 |
| WO | WO 01/52781 | 7/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 01/87379 | 11/2001 |
| WO | WO 01/95840 | 12/2001 |
| WO | WO 03/015672 | 2/2003 |

OTHER PUBLICATIONS

Ambrus; *The Biphasic Nature and Temperature Dependence of the Activation of Human Plasminogen by Urokinase*; May 1979; pp. 339-347; Research Communications in Chemical Pathology and Pharmacology, vol. 24, No. 2.

Anon, "Automatic feedback instrumentation for hospital room utilizing microsensors," IBM Technical Disclosure Bulletin (abs.), 29(3): 1 page, Aug. 1986.

Behmann, F.W., et al.; << Heat Generation Control during Artificial Hypothermia: I: Experimental Examination of the Influence of Anesthetic Depth; Pflügers Archiv, Bd. 266, S. 408-421 (1958) (German article with English translation).

Behmann, F.W., et al.; Intravascular Cooling, a Method to Achieve Controllable Hypothermia; Pflügers Archive, vol. 263, pp. 145-165 (1956) (German article with English translation).

Behmann, F.W.; "Regulation of heat production in experimental hypothermia of homothermal animals"; Naunyn Schmiedebergs Arch Exp Pathol Pharmakol; 228 (1-2): 126-128 (1956). (German article with English translation).

Behmann, F.W.; "Heat Generation Control during Artificial Hypothermia, an article about the economic problem of trembling stages"; Pflügers Archive, vol. 263, pp. 166-187 (1956) (German article with English translation).

Behmann, F.W; "Heat Generation Control during Artificial Hypothermia: II. Theoretical Examinations"; Pflügers Archiv, Bd. 266, S. 422-446 (1958) (German article with English translation).

Benzinger, T.H.; *On Physical Heart Regulation and Sense of Temperature in Man*; Naval Medical Research Institute; Physiology; vol. 45; pp. 645-659; (Feb. 26, 1959).

Bigelo; *Hypothermia, its Possible Role in Cardiac Surgery*; Nov. 1959; pp. 849-866; Annals of Surgery, vol. 132, No. 5.

Brengelmann, George L.; *Specialized Brain Cooling in Humans?*; The FASEB Journal; vol. 7; pp. 1148-1153 (Sep. 1993).

Buggy, D., P. Higgins, C. Moran, F. O'Donovan, and M. McCarroll, *Clonidine at Induction Reduces Shivering after General Anesthesia*, 1997, pp. 263-67, Can. J. Anaesth., vol. 44, N. 3.

Cabanac, M., *Selective Brain Cooling and Thermoregulatory Set-Point*, 1998, pp. 3-13, Journ. of Basic & Clinical Physiology & Pharmacology, vol. 9, N. 1.

Cabanac, M.; *Selective Brain Cooling in Humans: fancy or fact?*; The FASEB Journal; vol. 7; pp. 1143-1147 (Sep. 1993).

Capogna, G. snd D. Celleno, *I. V. Clonidine for post-Extradural Shivering in Parturients: A Preliminary Study*, 1993, Brit. Journ. of Anaesth., vol. 71.

Carrol et al. "A comparison of measurements from a temporal artery thermometer and a pulmonary artery thermistor—preliminary results," Fax correspondence dated Oct. 19, 2001.

Cheatle; *Cryostripping the Long and Short Saphenous Veins*; Jan. 1993; one page; Br. J. Surg., vol. 80.

Cheng, C. et al. (1995), "Increasing Mean Skin Temperature Linearly Reduces the Core-Temperature Thresholds for Vasoconstriction and Shivering in Humans," Anesthesiology 82(5):1160-1168, May.

Colvett, K. T., A. F. Althausen, B. Bassi!, N.M. Heney, F.V. McGovern, H.H. Young, II, D.S. Kaugman, A.L. Zietman, and W.U. Shipley, *Opportunities with Combined Modality Therapy for Selec-* tive Organ Preservation in Muscle-Invasive Bladder Cancer, 1996, pp. 201-208, Journ. of Surgical Oncology, vol. 63.

DeFord et al. "Design and evaluation of closed-loop feedback control of minimum temperatures in human intracranial tumours treated with interstitial hyperthermia," *Med. & Biol. Eng. & Comput.* 29:197-206, Mar. 1991.

Deklunder, G., M. Dauzat, J-L. Lecroart, J-J. Hauser, and Y. Houdas, "Influence of Ventilation of the Face on Thermoregulation in Man during Hyper- and Hypothermia," *Eur. J. Appl. Physiol.*, 1991, 62:342-348.

Dexter; *Blood Warms as it Blows Retrograde from a Femoral Cannulation Site to the Carotid Artery During Cardiopulmonary Bypass*; Nov. 1994; pp. 393-397; Perfusion, vol. 9, No. 6.

Gentilello, L. M., "Advances in the Management of Hypothermia," *Horizons in Trauma Surgery*, Apr. 1995, 75(2):243-256.

Gillinov; *Superior Cerebral Protection with Profound Hypothermia During Circulatory Arrest*; Nov. 1992; pp. 1432-1439; Ann. Thorac. Surg., vol. 55.

Giuffre, M. et al. (1991), "Rewarming Postoperative Patients: Lights, Blankets, or Forced Warm Air," *Journal of Post Anesthesia Nursing*, 6(6):386-393, December.

Guffin, Anita, et al.; "Shivering Following Cardiac Surgery: Hemodynamic Changes and Reversal."; Journal of Cardiothoracic Anesthesia; (Feb. 1987); pp. 24-28; vol. 1, No. 1.

Haley, E. C. et al. "A Randomized Trial of Tirilazad Mesylate in Patients with Acute Stroke (RANTTAS)," *Stroke*, 1996, 27(9):1453-1458.

Hederer, G., et al.; "Animal Experiment Observations Regarding Cardiac Surgery under Intravascular Hypothermia"; Labgebbecjs Arch. U. Dtsch. A. Chir., Bd. 283, S. 601-625 (1957) (German article with English translation).

Higazi; *The Effect of Ultrasonic Irradiation and Temperature on Fibrinolytic Activity in Vitro*; Aug. 1992; p. 251-253; Thrombosis Research, vol. 69, No. 2.

Iaizzo; *Facial Warming Increases the Threshold for Shivering*, 1999, Journal of Neurosurgical Anesthesiology, vol. 11, No. 4, pp. 231-239.

Imamaki; *Retrograde Cerebral Perfusion with Hypothermic Blood Provides Efficient Protection of the Brain*; Jul. 1995; pp. 325-333; Journal of Cardiac Surgery, vol. 10, No. 4, Part 1.

Jackson, Donald, et al; "Hypothermia : IV. Study of Hypothermia Induction Time with Various Pharmacological Agents (24617)"; Proc Soc Exp Biol Med.; 100(2): 332-335 (Feb. 1959).

Jessen et al., *Intravascular Heat Exchanger for Conscious Goats*, 1977.

Jolin; *Management of a Giant Intracranial Aneurysm Using Surface-Heparinized Extracorporeal Circulation and Controlled Deep Hypothermic Low Flow Perfusion*; Aug. 1992; pp. 756-760; Acta Anaesthesiologica Scandinavia.

Jos R.C. Jansen, Ph.D., et al. (1997) *Near continuous cardiac output by thermodilution*. Journal of Clinical Monitoring 13:233-239.

Keegan, M. T. et al. "Shivering Complicating the Treatment of Neurologically Impaired Surgical and Intensive Care Unit Patients," *Anesthesiology*, Sep. 1999, 91(3):874-876.

Kimoto; *Open Heart Surgery under Direct Vision with the Aid of Brain-Cooling by Irrigation*; Jul. 1955; pp. 592-603; Surgery, vol. 39, No. 4.

Kogaku "Sensor technology to control artificial organs," *KLA*, 22(4):295-300, Aug. 1984 (in Japanese).

Kurz, Martin, et al.; "Naloxone, Meperidine, and Shivering."; Anesthesiology; (Dec. 1983); pp. 1193-1201; V. 79; No. 6.

Lennon, R. L., M.P. Hosking, M.A. Conover, and W.J. Perkins, *Evaluation of Forced-Air System for Warming Hypothermic Postoperative Patients*, 1990, pp. 424-427, Anesth. Analg., vol. 70.

Leslie, K., D. I. Sessler, A. R. Bjorksten, M. Ozaki, T. Matsukawa, and M. Schroeder, *Propofol Causes a Dose-Dependent Decrease in the Thermoregulatory Threshold for vasoconstriction but has Little Effect on Sweating*, Aug. 1994, pp. 353-360, vol. 81, N. 2.

Maas, C. *Intermittent Antegrade Selective Cerebral Perfusion during Circulatory Arrest for Repair of Aortic Arch*. Perfusion, vol. 12, No. 2, pp. 127-132, 1997.

Marekovic, Z.; *Abstract of Renal Hypothermia in Situ by Venous Passages: Experimental Work on Dogs*; 1980; Eur Urol 6(2); 1 page.

Matsukawa, T., A. Kurz, D. I. Sessler, A. R. Bjorksten, B. Merrifield, and C. Cheng, *Propofol Linearly Reduces the Vasoconstriction and Shivering Thresholds*, May 1995, pp. 1169-1180, Anesthesiology, vol. 82, N. 5.

Meden, P., K. Overgaard, H. Pedersen, G. Boysen, *Effect of Hypothermia and Delayed Thrombolysis in a Rat Embolic Stroke Model*, 1994, pp. 91-98, Acta Neurol. Scand. vol. 90.

Meden; *The Influence of Body Temperature on Infarct Volume and Thrombolytic Therapy in a Rat Embolic Stroke Model*; Feb. 1994; pp. 131-138; Brain Research, vol. 647.

Mercer and Jessen, *Effects of Total Body Core Cooling on Heat Production of Conscious Goats*, 1978.

Milleret; Abstract of *Cryosclerosis of the Saphenous Veins in Varicose Reflux in the Obese and Elderly*, 10.1981; one page; Phlebologie, vol. 34, No. 4.

Möller et al. "Temperature control and light penetration in a feedback interstitial laser thermotherapy system," *Int. J. Hyperthermia*, 12(1):49-63, 1996.

Olshausen et al. "An isothermal flowmeter with improved frequency response for measuring tissue blood flow," *Pflügers Arch.* 367:97-102, 1976.

Pais, S. O., K. D. Tobin, C. B. Austin, and L. Queral, *Percutaneous Insertion of the Greenfield Inferior Vena Cava Filter: Experience with Ninety-Six Patients*, Oct. 1988, pp. 460-464, Journ. of Vascular Surg., vol. 8, N. 4.

Parkins; *Brain Cooling in the Prevention of Brain Damage During Periods of Circulatory Occlusion in Dogs*; Apr. 1954; pp. 284-289; Annals of Surgery, vol. 140, No. 3.

Patton, J. H, T. C. Fabian, M. A. Croce, G. Minard, F. E. Pritchard, and K. A. Kudsk, *Prophylactic Greenfield Filters: Acute Complications and Long-Term Follow-Up*, Aug. 1996; pp. 231-237; Journ. of Trauma: Injury, Infection, and Critical Care, vol. 41, N. 2.

Piepgras; *Rapid Active Internal Core Cooling for Induction of Moderate Hypothermia in Head Injury by Use of an Extracorporeal Heat Exchanger*; Feb. 1998; pp. 311-318; Neurosurgery, vol. 42, No. 2.

Rijken; *Plasminogen Activation at Low Temperatures in Plasma Samples Containing Therapeutic Concentrations of Tissue-Type Plasminogen Activator or Other Thrombolytic Agents*; Oct. 1989; pp. 47-52; place of publication unknown.

Rohrer, M. J. and A. M. Natale, *Effect of Hypothermia on the Coagulation Cascade*, Oct. 1992, pp. 1402-1405, Critical Care Medicine, vol. 20, N. 10.

Schmid-Elsaesser, R. et al. (1999), *Combination Drug Therapy and Mild Hypothermia: A Promising Treatment Strategy for Reversible, Focal Cerebral Ischemia*, Stroke, 1891-1899, June.

Schwartz, A.E. et al.; (1996); *Isolated cerebral hypothermia by single carotid artery perfusion of extracorporeally cooled blood in baboons*; Neurosurgery 39(3):577-582.

Schwartz; *Cerebral Blood Flow during Low-flow Hypothermic Cardiopulmonary Bypass in Baboons*; Jun. 1994; pp. 959-964; Anesthesiology, vol. 81, No. 4.

Schwartz; *Selective Cerebral Hypothermia by Means of Transfemoral Internal Carotid Artery Catheterization*; May 1996; pp. 571-572; Radiology, vol. 201, No. 2.

Sessler, Daniel I.; "Mild Perioperative Hypothermia"; The New England Journal of Medicine; pp. 1730-1737; 336:1730-1737; (Jun. 12, 1997).

Sharkey, A., J. M. Lipton, M. T. Murphy, and A. H. Giesecke, *Inhibition of Postanesthestic Shivering with Radiant Heat*, Feb. 1987, pp. 249-252, Anesthesiology, vol. 66, N. 2.

Shiraki, K., N. Konda, and S. Sagawa, Esphageal and Tympanic Temperature Responses to Core Blood Temperature Changes during Hyperthermia, *J. Appl. Physiol.* 61(1):98-102 (1986).

Simon, M., C. A. Athanasoulis, D. Kim, F. L. Steinberg, D. H Porter, B. H. Byse, S. Kleshinski, S. Geller, D. E. Orron, and A. C. Waltman; *Simon Nitinol Inferior Vena Cava Filter: Initial Clinical Experience*, Jul. 1989, pp. 99-103; Radiology.

Steen; *The Detrimental Effects of Prolonged Hypothermia and Rewarming in the Dog*; Aug. 1979 ;pp. 224-230; Anesthesiology, vol. 52, No. 3.

Vandam; *Hypothermia*; Sep. 1959; pp. 546-553; The New England Journal of Medicine.

Villamaria, F. J., C. E. Baisden, A. Hillis, M. H. Rajab, and P. A. Rinaldi, "Forced-Air Warming is no More Effective than Conventional Methods for Raising Postoperative Core Temperature After Cardiac Surgery," *Journ. Cardiothoracic and Vascular Anesth.*, Oct. 1997, 11(6):708-711.

White; Cerebral *Hypothermia and Circulatory Arrest*; Jul. 1978; pp. 450-458; Mayo Clinic Proceedings, vol. 53.

Williams et al., *Passivity breakdown and pitting corrosion of binary alloys*, 1991.

Yenari; *Thrombolysis with Tissue Plasminogen Activator (TPA) is Temperature Dependent*; Jul. 1994; pp. 475-481; Thrombosis Research, vol. 77, No. 5.

Yoshihara; *Changes in Coagulation and Fibrinolysis Occurring in Dogs during Hypothermia*; Aug. 1984; pp. 503-512; Thrombosis Research, vol. 37, No. 4.

Zarins; *Circulation in Profound Hypothermia*; Nov. 1972; pp. 97-104; Journal of Surgical Research, vol. 14, N. 2.

Zweifler, R. M. and D. I. Sessler, "Thermoregulatory Vasoconstriction and Shivering Impede Therapeutic Hypothermia in Acute Ischemic Stroke Patients," *Journ. Stroke and Cerebrovascular Diseases*, 1996, 6(2):100-104.

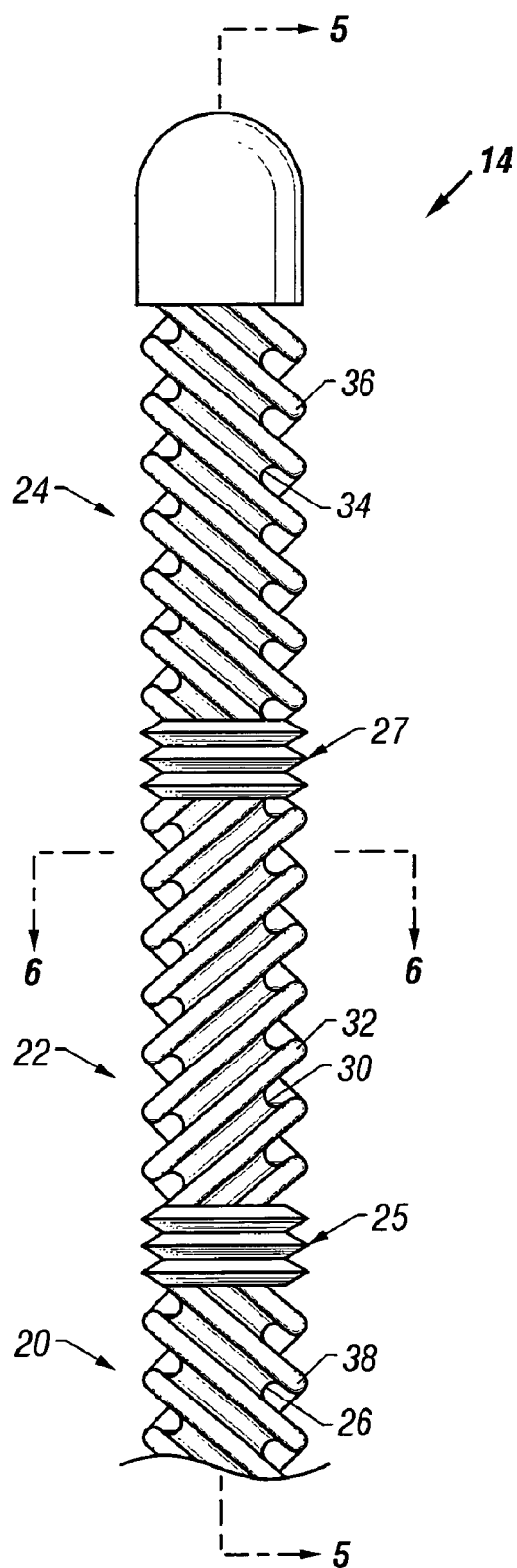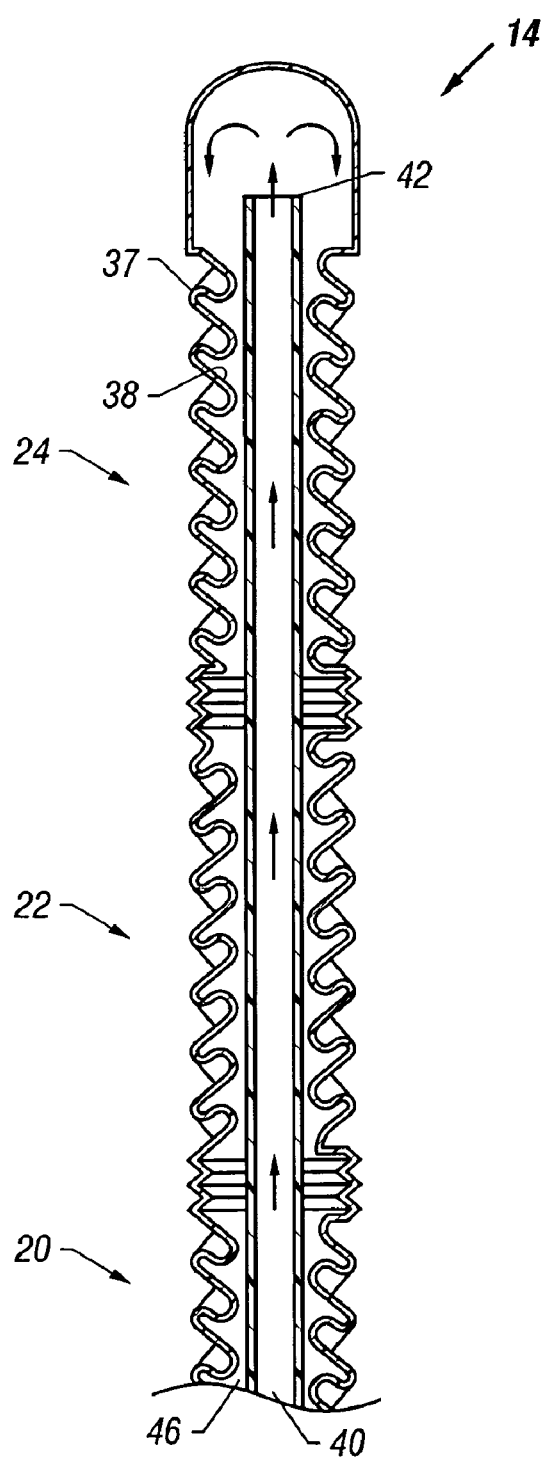
*FIG. 4*   *FIG. 5*

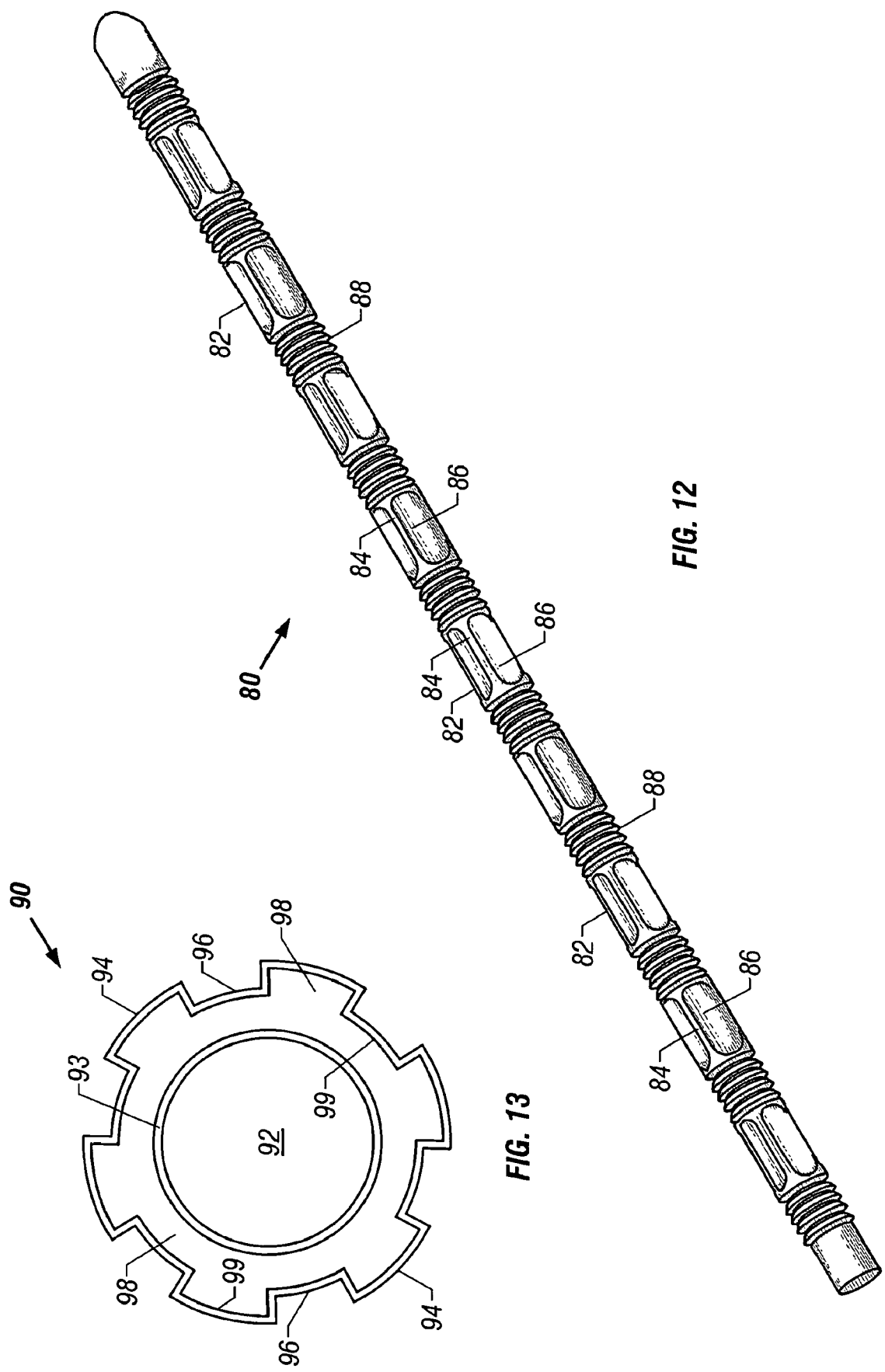

SELECTIVE ORGAN COOLING APPARATUS

CROSS REFERENCE TO RELATED APPLICATIONS

This is a continuation patent application of U.S. patent application Ser. No. 10/796,906, now U.S. Pat. No. 7,066,948, filed on Mar. 8, 2004, and entitled "Selective Organ Cooling Apparatus and Method"; which is a continuation patent application of U.S. patent application Ser. No. 10/161,107, filed on May 30, 2002, and entitled "Selective Organ Cooling Apparatus and Method" now U.S. Pat. No. 6,702,842; which is a continuation patent application of U.S. patent application Ser. No. 09/607,799, filed on Jun. 30, 2000 now U.S. Pat. No. 6,464,716, and entitled "Selective Organ Cooling Apparatus and Method"; which is a continuation-in-part patent application of U.S. patent application Ser. No. 09/570,075, filed on May 12, 2000, and entitled "Selective Organ Cooling Apparatus and Method" now U.S. Pat. No. 6,471,717; a continuation-in-part patent application of U.S. patent application Ser. No. 09/215,041, filed on Dec. 16, 1998, and entitled "Articulation Device for Selective Organ Cooling Apparatus", now U.S. Pat. No. 6,254,626; a continuation-in-part patent application of U.S. patent application Ser. No. 09/103,342, filed on Jun. 23, 1998, and entitled "Selective Organ Cooling Catheter and Method of Using the Same", now U.S. Pat. No. 6,096,068; a continuation-in-part patent application of U.S. patent application Ser. No. 09/052,545, filed on Mar. 31, 1998, and entitled "Circulating Fluid Hypothermia Method and Apparatus", now U.S. Pat. No. 6,231,595; and a continuation-in-part patent application of U.S. patent application Ser. No. 09/047,012, filed on Mar. 24, 1998, and entitled "Selective Organ Hypothermia Method and Apparatus", now U.S. Pat. No. 5,957,963; and a continuation-in-part patent application of U.S. patent application Ser. No. 09/012,287, filed on Jan. 23, 1998, and entitled "Selective Organ Hypothermia Method and Apparatus", now U.S. Pat. No. 6,051,019. The disclosures of these parent applications are hereby incorporated herein by reference.

STATEMENT REGARDING FEDERALLY SPONSORED RESEARCH OR DEVELOPMENT

Not Applicable

BACKGROUND OF THE INVENTION

1. Field of the Invention

The present invention relates generally to the modification and control of the temperature of a selected body organ. More particularly, the invention relates to a method and intravascular apparatus for controlling organ temperature.

2. Background Art

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. However, the use of total body hypothermia risks certain deleterious systematic vascular effects. For example, total body hypothermia may cause severe derangement of the cardiovascular system, including low cardiac output, elevated systematic resistance, and ventricular fibrillation. Other side effects include renal failure, disseminated intravascular coagulation, and electrolyte disturbances. In addition to the undesirable side effects, total body hypothermia is difficult to administer.

Catheters have been developed which are inserted into the bloodstream of the patient in order to induce total body hypothermia. For example, U.S. Pat. No. 3,425,419 to Dato describes a method and apparatus of lowering and raising the temperature of the human body. Dato induces moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. However, use of the Dato device implicates the negative effects of total body hypothermia described above.

Due to the problems associated with total body hypothermia, attempts have been made to provide more selective cooling. For example, cooling helmets or head gear have been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. In addition, when using conduction to cool the brain, the face of the patient is also subjected to severe hypothermia, increasing discomfort and the likelihood of negative side effects. It is known that profound cooling of the face can cause similar cardiovascular side effects as total body cooling. From a practical standpoint, such devices are cumbersome and may make continued treatment of the patient difficult or impossible.

Selected organ hypothermia has been accomplished using extracorporeal perfusion, as detailed by Arthur E. Schwartz, M. D. et al., in *Isolated Cerebral Hypothermia by Single Carotid Artery Perfusion of Extracorporeally Cooled Blood in Baboons*, which appeared in Vol. 39, No. 3, NEUROSURGERY 577 (September, 1996). In this study, blood was continually withdrawn from baboons through the femoral artery. The blood was cooled by a water bath and then infused through a common carotid artery with its external branches occluded. Using this method, normal heart rhythm, systemic arterial blood pressure and arterial blood gas values were maintained during the hypothermia. This study showed that the brain could be selectively cooled to temperatures of 20° C. without reducing the temperature of the entire body. However, external circulation of blood is not a practical approach for treating humans because the risk of infection, need for anticoagulation, and risk of bleeding is too great. Further, this method requires cannulation of two vessels making it more cumbersome to perform particularly in emergency settings. Even more, percutaneous cannulation of the carotid artery is difficult and potentially fatal due to the associated arterial wall trauma. Finally, this method would be ineffective to cool other organs, such as the kidneys, because the feeding arteries cannot be directly cannulated percutaneously.

Selective organ hypothermia has also been attempted by perfusion of a cold solution such as saline or perfluorocarbons. This process is commonly used to protect the heart during heart surgery and is referred to as cardioplegia. Perfusion of a cold solution has a number of drawbacks, including a limited time of administration due to excessive volume accumulation, cost, and inconvenience of maintaining the perfusate and lack of effectiveness due to the temperature dilution from the blood. Temperature dilution by the blood is a particular problem in high blood flow organs such as the brain.

Therefore, a practical method and apparatus which modifies and controls the temperature of a selected organ satisfies a long-felt need.

BRIEF SUMMARY OF THE INVENTION

The apparatus of the present invention can, by way of example only, include a heat transfer element which comprises first and second elongated, articulated segments, each segment can have either a turbulence-inducing or mixing-inducing exterior surface or a smooth exterior surface. A flexible joint can connect the first and second elongated segments. An inner coaxial lumen may be disposed within the first and second elongated segments and is capable of transporting a pressurized working fluid to a distal end of the first elongated segment. In addition, the first and second elongated segments may have a turbulence-inducing or mixing-inducing interior surface for inducing turbulence or mixing within the pressurized working fluid. The turbulence-inducing or mixing-inducing exterior surface may be adapted to induce turbulence or mixing within a free stream of blood flow when placed within an artery. The turbulence-inducing exterior surface may be adapted to induce a turbulence intensity greater than 0.05 within a free stream blood flow. In one embodiment, the flexible joint comprises a bellows section which also allows for axial compression of the heat transfer element. In another embodiment, the flexible joint comprises a straight, flexible tube as disclosed in U.S. patent application Ser. No. 09/215,041, filed on Dec. 16, 1998, and entitled "Articulation Device for Selective Organ Cooling Apparatus", the disclosure of which is entirely incorporated herein by reference.

In one embodiment, the turbulence-inducing or mixing-inducing exterior surfaces of the heat transfer element comprise one or more alternating ridges and grooves. The ridges and grooves can be aligned longitudinally along the heat transfer element, or they can be arranged helically around the heat transfer element. Where straight ridges and grooves are used, adjacent segments can have their ridges angularly offset from each other, to increase turbulence or mixing. Similarly, where helical ridges are used, adjacent segments of the heat transfer element can be oppositely spiraled, to increase turbulence or mixing. For instance, the first elongated heat transfer segment may comprise one or more helical ridges having a counter-clockwise twist, while the second elongated heat transfer segment comprises one or more helical ridges having a clockwise twist. Alternatively, of course, the first elongated heat transfer segment may comprise one or more clockwise helical ridges, and the second elongated heat transfer segment may comprise one or more counter-clockwise helical ridges.

The first and second elongated, articulated segments may be formed from highly conductive materials, such as a metal, or a polymer doped or loaded with particles or filaments of a conductive material. Where the surface has sufficiently pronounced features such as ridges, the enhanced surface area alone may provide sufficient heat transfer, without a need for angular offsets, or opposite spirals, to induce turbulence or mixing.

In another embodiment, the turbulence-inducing or mixing-inducing exterior surface of the heat transfer element is adapted to induce turbulence or mixing throughout the duration of each pulse of a pulsatile blood flow when placed within an artery. In still another embodiment, the turbulence-inducing or mixing-inducing exterior surface of the heat transfer element is adapted to induce turbulence or mixing during at least 20% of the period of each cardiac cycle when placed within an artery.

In yet another embodiment, the exterior surface of the heat transfer element may be an entirely smooth surface, such as a right circular cylinder. The segments of the heat transfer element can have a smooth exterior surface, where the surface area is large enough to provide sufficient heat transfer. Here again, the articulated segments may be formed from highly conductive materials, such as a metal, or a polymer doped or loaded with particles or filaments of a conductive material.

The heat transfer device may also have a coaxial supply catheter with an inner catheter lumen coupled to the inner coaxial lumen within the first and second elongated heat transfer segments. A working fluid supply configured to dispense the pressurized working fluid may be coupled to the inner catheter lumen. The working fluid supply may be configured to produce the pressurized working fluid at a temperature of about 0° C. and at a pressure below about 5 atmospheres of pressure.

In yet another alternative embodiment, the heat transfer device may have three or more elongated, articulated, heat transfer segments having a turbulence-inducing, mixing-inducing, or smooth exterior surface, with additional flexible joints connecting the additional elongated heat transfer segments. In one such embodiment, by way of example, the first and third elongated heat transfer segments may comprise clockwise helical ridges, and the second elongated heat transfer segment may comprise one or more counter-clockwise helical ridges. Alternatively, of course, the first and third elongated heat transfer segments may comprise counter-clockwise helical ridges, and the second elongated heat transfer segment may comprise one or more clockwise helical ridges. As still another alternative, in the use of longitudinal ridges, the second elongated heat transfer segment may have longitudinal ridges offset by a radial angle from the longitudinal ridges on the first segment, and the third heat transfer segment may have longitudinal ridges offset by a radial angle from the longitudinal ridges on the second segment. As yet another alternative, of course, each elongated heat transfer segment can be a smooth right circular cylinder. Further, a mixture of these types of elongated heat transfer segments can be used on a heat transfer device.

The turbulence-inducing, mixing-inducing, or smooth exterior surface of the heat transfer element may optionally include a surface coating or treatment to inhibit clot formation. One variation of the heat transfer element comprises a stent coupled to a distal end of the first elongated heat transfer segment.

The present invention also envisions a method of treating the brain which comprises the steps of inserting a flexible, conductive heat transfer element into a carotid artery from a distal location, and circulating a working fluid through the flexible, conductive heat transfer element in order to selectively modify the temperature of the brain without significantly modifying the temperature of the entire body. The flexible, conductive heat transfer element preferably absorbs more than about 25, 50 or 75 Watts of heat.

The method may also comprise the step of inducing turbulence or mixing within the free stream blood flow within the carotid artery. In one embodiment, the method includes the step of inducing blood turbulence with a turbulence intensity greater than about 0.05 within the carotid artery. In another embodiment, the method includes the step of inducing blood turbulence or mixing throughout the duration of the period of the cardiac cycle within the carotid artery. In yet another embodiment, the method comprises the step of inducing blood turbulence or mixing throughout the period of the cardiac cycle within the carotid artery or during greater than about 20% of the period of the cardiac cycle within the carotid artery. The step of circulating may comprise the step of inducing turbulent flow or mixing of the working fluid through the flexible, conductive heat transfer element. The pressure of the working fluid may be maintained below about 5 atmospheres of pressure.

The present invention also envisions a method for selectively cooling an organ in the body of a patient which comprises the steps of introducing a catheter, with a heat transfer element, into a blood vessel supplying the organ, the catheter having a diameter of about 4 mm or less, inducing free stream turbulence or mixing in blood flowing over the heat transfer element, and cooling the heat transfer element to remove heat from the blood to cool the organ without substantially cooling the entire body. In one embodiment, the cooling step removes at least about 75 Watts of heat from the blood. In another embodiment, the cooling step removes at least about 100 Watts of heat from the blood. The organ being cooled may be the human brain.

The step of inducing free stream turbulence may induce a turbulence intensity greater than about 0.05 within the blood vessel. The step of inducing free stream turbulence may induce turbulence throughout the duration of each pulse of blood flow. The step of inducing free stream turbulence may induce turbulence for at least about 20% of the duration of each pulse of blood flow.

In one embodiment, the catheter has a flexible metal, or doped polymer, tip and the cooling step occurs at the tip. The tip may have smooth, turbulence-inducing, or mixing-inducing elongated heat transfer segments separated by bellows sections. The turbulence-inducing or mixing-inducing segments may comprise longitudinal or helical ridges which are configured to have a depth which is greater than a thickness of a boundary layer of blood which develops within the blood vessel. In another embodiment, the catheter has a tip at which the cooling step occurs and the tip has turbulence-inducing or mixing-inducing elongated heat transfer segments that alternately spiral bias the surrounding blood flow in clockwise and counterclockwise directions.

The cooling step may comprise the step of circulating a working fluid in through an inner lumen in the catheter and out through an outer, coaxial lumen. In one embodiment, the working fluid remains a liquid throughout the cycle. The working fluid may be aqueous.

The present invention also envisions a cooling catheter comprising a catheter shaft having first and second lumens therein. The cooling catheter also comprises a cooling tip adapted to transfer heat to or from a working fluid circulated in through the first lumen and out through the second lumen, and either a smooth exterior surface or turbulence-inducing or mixing-inducing structures on the cooling tip capable of inducing free stream turbulence or mixing when the tip is inserted into a blood vessel. The turbulence-inducing structures may induce a turbulence intensity of at least about 0.05. The cooling tip may be adapted to induce turbulence or mixing within the working fluid. The catheter is capable of removing at least about 25 Watts of heat from an organ when inserted into a vessel supplying that organ, while cooling the tip with a working fluid that remains a liquid in the catheter. Alternatively, the catheter is capable of removing at least about 50 or 75 Watts of heat from an organ when inserted into a vessel supplying that organ, while cooling the tip with an aqueous working fluid. In one embodiment, in use, the tip has a diameter of about 4 mm or less. Optionally, the turbulence-inducing or mixing-inducing surfaces on the heat transfer segments comprise longitudinal or helical ridges which have a depth sufficient to disrupt the free stream blood flow in the blood vessel. Alternatively, the turbulence-inducing or mixing-inducing surfaces may comprise staggered protrusions from the outer surfaces of the heat transfer segments, which have a height sufficient to disrupt the free stream flow of blood within the blood vessel.

In another embodiment, a cooling catheter may comprise a catheter shaft having first and second lumens therein, a cooling tip adapted to transfer heat to or from a working fluid circulated in through the first lumen and out through the second lumen, and either a smooth exterior surface or turbulence-inducing or mixing-inducing structures on the cooling tip capable of inducing turbulence or mixing when the tip is inserted into a blood vessel. Alternatively, a cooling catheter may comprise a catheter shaft having first and second lumens therein, a cooling tip adapted to transfer heat to or from a working fluid circulated in through the first lumen and out through the second lumen, and structures on the cooling tip capable of inducing free stream turbulence or mixing when the tip is inserted into a blood vessel. In another embodiment, a cooling catheter may comprise a catheter shaft having first and second lumens therein, a cooling tip adapted to transfer heat to or from a working fluid circulated in through the first lumen and out through the second lumen, and turbulence-inducing structures on the cooling tip capable of inducing turbulence with an intensity greater than about 0.05 when the tip is inserted into a blood vessel.

The novel features of this invention, as well as the invention itself, will be best understood from the attached drawings, taken along with the following description, in which similar reference characters refer to similar parts, and in which:

BRIEF DESCRIPTION OF THE SEVERAL
VIEWS OF THE DRAWINGS

FIG. 4 is an elevation view of one embodiment of a heat transfer element according to the invention, with alternating helices;

FIG. 5 is longitudinal section view of the heat transfer element of FIG. 4;

FIG. 12 is a perspective view of a fourth embodiment of a heat transfer element according to the invention, with offset longitudinal ridges on adjacent segments; and FIG. 13 is a transverse section view of the heat transfer element of FIG. 11 or FIG. 12.

DETAILED DESCRIPTION OF THE INVENTION

Figure 1:
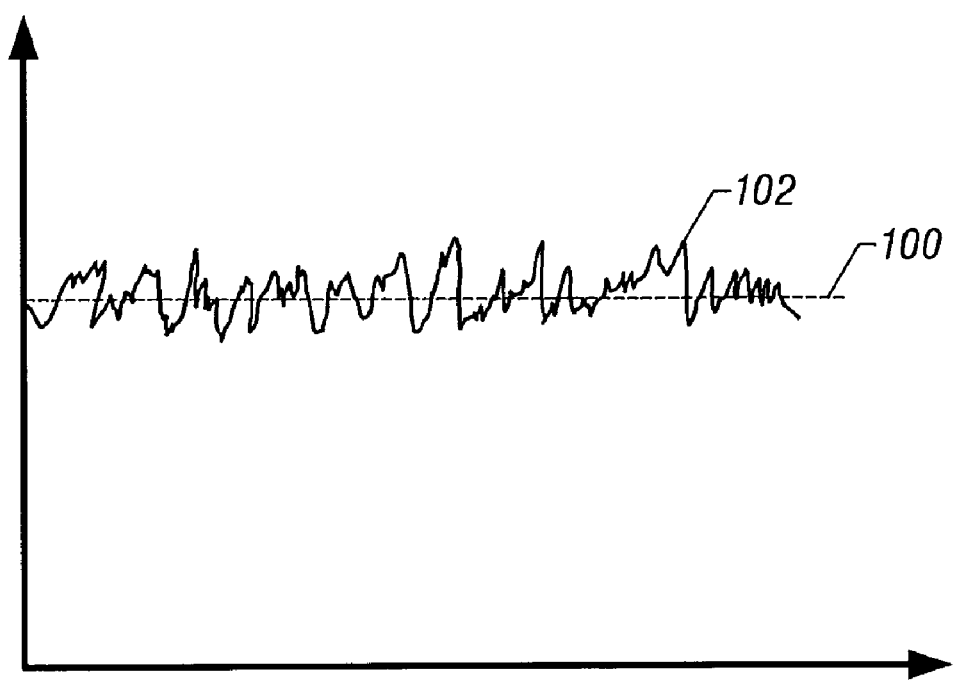
FIG. 1 is a graph illustrating the velocity of steady state turbulent flow as a function of time.

In order to intravascularly regulate the temperature of a selected organ, a heat transfer element may be placed in the feeding artery of the organ to absorb or deliver the heat from or to the blood flowing into the organ. The transfer of heat may cause either a cooling or a heating of the selected organ. The heat transfer element must be small enough to fit within the feeding artery while still allowing a sufficient blood flow to reach the organ in order to avoid ischemic organ damage. A heat transfer element which selectively cools an organ should be capable of providing the necessary heat transfer rate to produce the desired cooling or heating effect within the organ. By placing the heat transfer element within the feeding artery of an organ, the temperature of an organ can be controlled without significantly affecting the remaining parts of the body. These points can be illustrated by using brain cooling as an example.

The common carotid artery supplies blood to the head and brain. The internal carotid artery branches off of the common carotid to directly supply blood to the brain. To selectively cool the brain, the heat transfer element is placed into the common carotid artery, or both the common carotid artery and the internal carotid artery. The internal diameter of the common carotid artery ranges from 6 to 8 mm and the length ranges from 80 to 120 mm. Thus, the heat transfer element residing in one of these arteries cannot be much larger than 4 mm in diameter in order to avoid occluding the vessel.

It is important that the heat transfer element be flexible in order to be placed within the small feeding artery of an organ. Feeding arteries, like the carotid artery, branch off the aorta at various levels. Subsidiary arteries continue to branch off the initial branches. For example, the internal carotid artery is a small diameter artery that branches off of the common carotid artery near the angle of the jaw. Because the heat transfer element is typically inserted into a peripheral artery, such as the femoral artery, and accesses the feeding artery by initially passing though a series of one or more of these branches, the flexibility of the heat transfer element is an important characteristic of the heat transfer element. Further, the heat transfer element is ideally constructed from a highly thermally conductive material such as metal, or a metal-doped polymer, in order to facilitate heat transfer. The use of a highly thermally conductive material increases the heat transfer rate for a given temperature differential between the coolant within the heat transfer element and the blood. This facilitates the use of a higher temperature coolant within the heat transfer element, allowing safer coolants, such as water, to be used. Highly thermally conductive materials, such as metals, tend to be rigid. Therefore, the design of the heat transfer element should facilitate flexibility in an inherently inflexible material. Alternatively, the heat transfer element can be constructed of a flexible polymer doped or loaded with particles or filaments of a conductive material, such as a metal.

In order to obtain the benefits of hypothermia described above, it is desirable to reduce the temperature of the blood flowing to the brain to between 30° C. and 32° C. Given that a typical brain has a blood flow rate through each carotid artery (right and left) of approximately 250-375 cubic centimeters per minute, the heat transfer element should absorb 75-175 Watts of heat when placed in one of the carotid arteries, in order to induce the desired cooling effect. It should be noted that smaller organs may have less blood flow in the supply artery and may require less heat transfer, such as 25 Watts.

When a heat transfer element is inserted coaxially into an artery, the primary mechanism of heat transfer between the surface of the heat transfer element and the blood is forced convection. Convection relies upon the movement of fluid to transfer heat. Forced convection results when an external force causes motion within the fluid. In the case of arterial flow, the beating heart causes the motion of the blood around the heat transfer element.

The magnitude of the heat transfer rate is proportional to the surface area of the heat transfer element, the temperature differential, and the heat transfer coefficient of the heat transfer element.

As noted above, the receiving artery into which the heat transfer element is placed has a limited diameter and length. Thus, surface area of the heat transfer element must be limited, to avoid significant obstruction of the artery, and to allow the heat transfer element to easily pass through the vascular system. For placement within the internal and common carotid artery, the cross sectional diameter of the heat transfer element is limited to about 4 mm, and its length is limited to approximately 10 cm.

The temperature differential can be increased by decreasing the surface temperature of the heat transfer element. However, the minimum allowable surface temperature is limited by the characteristics of blood. Blood freezes at approximately 0° C. When the blood approaches freezing, ice emboli may form in the blood which may lodge downstream, causing serious ischemic injury. Furthermore, reducing the temperature of the blood also increases its viscosity, which results in a small decrease in the value of the convection heat transfer coefficient. In addition, increased viscosity of the blood may result in an increase in the pressure drop within the artery, thus, compromising the flow of blood to the brain. Given the above constraints, it is advantageous to limit the minimum allowable surface temperature of the heat transfer element to approximately 5° C. This results in a maximum temperature differential between the blood stream and the heat transfer element of approximately 32° C.

The mechanisms by which the value of the convection heat transfer coefficient may be increased are complex. A heat transfer element with a smooth exterior surface may be able to provide the desired amount of heat transfer. However, it is well known that the convection heat transfer coefficient increases with the level of turbulent kinetic energy in the fluid flow. Thus, if flow past a smooth heat transfer element will not transfer sufficient heat, it is advantageous to have turbulent or otherwise mixed blood flow in contact with the heat transfer element.

FIG. 1 is a graph illustrating steady state turbulent flow. The vertical axis is the velocity of the flow. The horizontal axis represents time. The average velocity of the turbulent flow is shown by a line 100. The actual instantaneous velocity of the flow is shown by a curve 102.

Figure 3C:
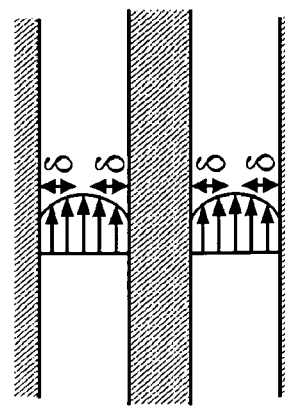
FIG. 3C is a velocity profile diagram showing blood flow velocity within an artery, averaged over the duration of the cardiac pulse, after insertion of a smooth heat transfer element within the artery.
Figure 3B:
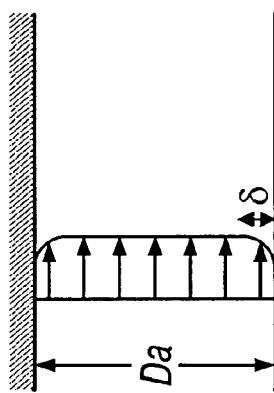
FIG. 3B is a velocity profile diagram showing blood flow velocity within an artery, averaged over the duration of the cardiac pulse.
Figure 3A:
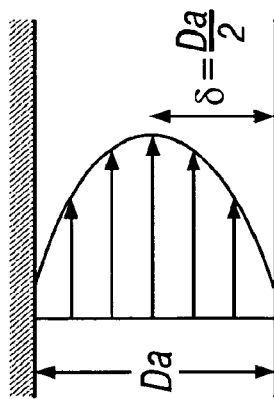
FIG. 3A is a velocity profile diagram showing a typical steady state Poiseuillean flow driven by a constant pressure gradient.

Under constant pressure conditions, steady flows in pipes are characterized as a balance between viscous stresses and the constant pressure gradient. Such flows are called Poiseuillean. FIG. 3A is a velocity profile diagram showing a typical steady state Poiseuillean flow driven by a constant pressure gradient. The velocity of the fluid across the pipe is shown in FIG. 3A by the parabolic curve and corresponding velocity vectors. The velocity of the fluid in contact with the wall of the pipe is zero. The boundary layer is the region of the flow in contact with the pipe surface in which viscous stresses are dominant. In steady state Poiseuillean flow, the boundary layer develops until it includes the whole pipe, i.e., the boundary layer thickness in FIG. 3A is one half of the diameter of the pipe.

Under conditions of Poiseuillean flow, the Reynolds number, the ratio of inertial forces to viscous forces, can be used to characterize the level of turbulent kinetic energy existing in the flow. For Poiseuillean flows, Reynolds numbers must be greater than about 2300 to cause a transition from laminar to turbulent flow. Further, when the Reynolds number is greater than about 2000, the boundary layer is receptive to "tripping". Tripping is a process by which a small perturbation in the boundary layer can create turbulent conditions. The receptivity of a boundary layer to "tripping" is proportional to the Reynolds number and is nearly zero for Reynolds numbers less than 2000.

Figure 2A:
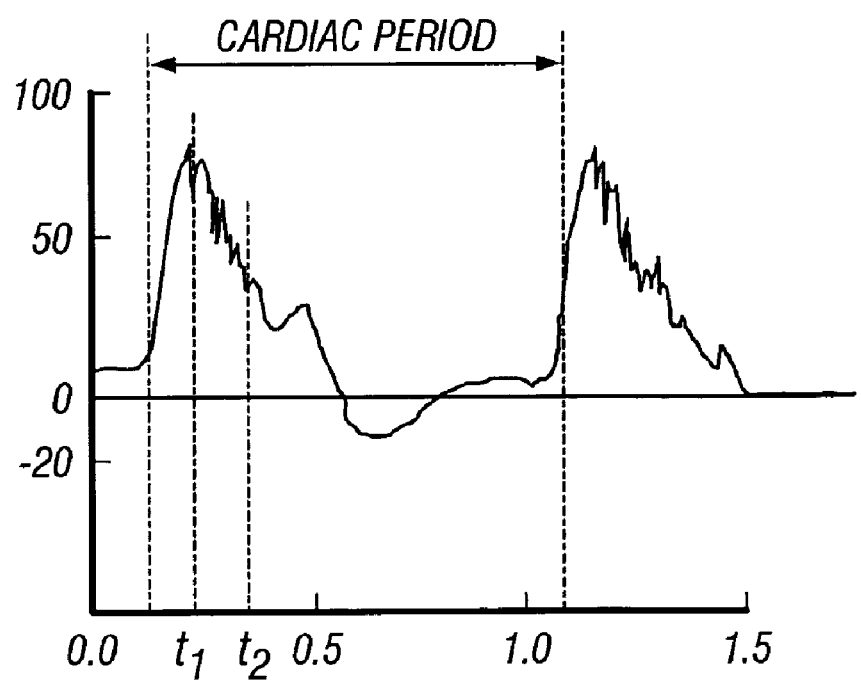
FIG. 2A is a graph showing the velocity of the blood flow within an artery as a function of time.

In contrast with the steady Poiseuillean flow, the blood flow in arteries is induced by the beating heart and is therefore pulsatile. FIG. 2A is a graph showing the velocity of the blood flow within an artery as a function of time. The beating heart provides pulsatile flow with an approximate period of 0.5 to 1 second. This is known as the period of the cardiac cycle. The horizontal axis in FIG. 2A represents time in seconds and the vertical axis represents the average velocity of blood in centimeters per second. Although very high velocities are reached at the peak of the pulse, the high velocity occurs for only a small portion of the cycle. In fact, the velocity of the blood reaches zero in the carotid artery at the end of a pulse and temporarily reverses.

Because of the relatively short duration of the cardiac pulse, the blood flow in the arteries does not develop into the classic Poiseuillean flow. FIG. 3B is a velocity profile diagram showing blood flow velocity within an artery averaged over the cardiac pulse. The majority of the flow within the artery has the same velocity. The boundary layer where the flow velocity decays from the free stream value to zero is very thin, typically $\frac{1}{6}$ to $\frac{1}{20}$ of the diameter of the artery, as opposed to one half of the diameter of the artery in the Poiseuillean flow condition.

As noted above, if the flow in the artery were steady rather than pulsatile, the transition from laminar to turbulent flow would occur when the value of the Reynolds number exceeds about 2,000. However, in the pulsatile arterial flow, the value of the Reynolds number varies during the cardiac cycle, just as the flow velocity varies. In pulsatile flows, due to the enhanced stability associated with the acceleration of the free stream flow, the critical value of the Reynolds number at which the unstable modes of motion grow into turbulence is found to be much higher, perhaps as high as 9,000.

The blood flow in the arteries of interest remains laminar over more than 80% of the cardiac cycle. Referring again to FIG. 2A, the blood flow is turbulent from approximately time $t_1$ until time $t_2$ during a small portion of the descending systolic flow, which is less than 20% of the period of the cardiac cycle. If a heat transfer element is placed inside the artery, heat transfer will be facilitated during this short interval. However, to transfer the necessary heat to cool the brain turbulent kinetic energy should be produced in the blood stream and sustained throughout the entire period of the cardiac cycle.

A thin boundary layer has been shown to form during the cardiac cycle. This boundary layer will form over the surface of a smooth heat transfer element. FIG. 3C is a velocity profile diagram showing blood flow velocity within an artery, averaged over the cardiac pulse, after insertion of a smooth heat transfer element within the artery. In FIG. 3C, the diameter of the heat transfer element is about one half of the diameter of the artery. Boundary layers develop adjacent to the heat transfer element as well as next to the walls of the artery. Each of these boundary layers has approximately the same thickness as the boundary layer which would have developed at the wall of the artery in the absence of the heat transfer element. The free stream flow region is developed in an annular ring around the heat transfer element. Blood flow past such a smooth heat transfer element may transfer sufficient heat to accomplish the desired temperature control.

One way to increase the heat transfer rate is to create a turbulent boundary layer on the heat transfer element surface. However, turbulence in the very thin boundary layer will not produce sufficient kinetic energy to produce the necessary heat transfer rate. Therefore, to induce sufficient turbulent kinetic energy to increase the heat transfer rate sufficiently to cool the brain, a stirring mechanism, which abruptly changes the direction of velocity vectors, should be utilized. This can create high levels of turbulence intensity in the free stream, thereby sufficiently increasing the heat transfer rate.

This turbulence intensity should ideally be sustained for a significant portion of the cardiac cycle. Further, turbulent kinetic energy should ideally be created throughout the free stream and not just in the boundary layer. FIG. 2B is a graph illustrating the velocity of continually turbulent flow under pulsatile conditions as a function of time, which would result in optimal heat transfer in arterial blood flow. Turbulent velocity fluctuations are seen throughout the cycle as opposed to the short interval of fluctuations seen in FIG. 2A between time $t$, and time $t_2$. These velocity fluctuations are found within the free stream. The turbulence intensity shown in FIG. 2B is at least 0.05. In other words, the instantaneous velocity fluctuations deviate from the mean velocity by at least 5%. Although, ideally, turbulence or mixing is created throughout the entire period of the cardiac cycle, the benefits of turbulence are also obtained if the turbulence or mixing is sustained for only 75%, 50% or even as low as 30% or 20% of the cardiac cycle.

To create the desired level of turbulence intensity or mixing in the blood free stream during the whole cardiac cycle, one embodiment of the invention uses a modular design. This design creates helical blood flow and produces a high level of mixing in the free stream.

For a swirling flow in a tube in which the azimuthal velocity of the fluid vanishes toward the stationary outer boundary, any non-vanishing azimuthal velocity in the interior of the flow will result in an instability in which the inner fluid is spontaneously exchanged with fluid near the wall, analogous to Taylor cells in the purely azimuthal flow between a rotating inner cylinder and stationary outer cylinder. This instability results from the lack of any force in opposition to the centripetal acceleration of the fluid particles moving along helical paths, the pressure in the tube being a function only of longitudinal position. In one embodiment, the device of the present invention imparts an azimuthal velocity to the interior of a developed pipe flow, with the net result being a continuous exchange of fluid between the core and perimeter of the flow as it moves longitudinally down the pipe. This fluid exchange enhances the transport of heat, effectively increasing the convective heat transfer coefficient over that which would have obtained in undisturbed pipe flow. This bulk exchange of fluid is not necessarily turbulent, although turbulence is possible if the induced azimuthal velocity is sufficiently high.

Figure 2C:
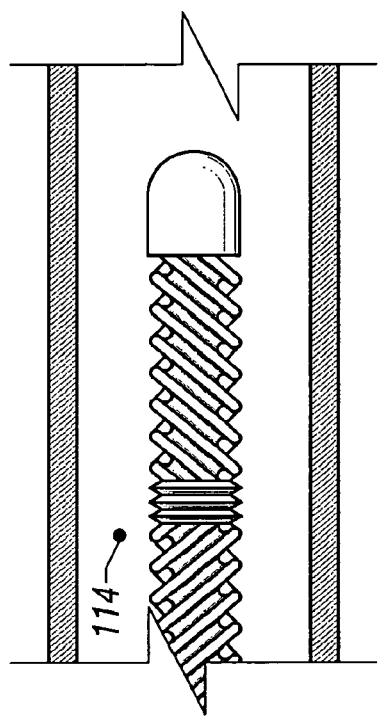
FIG. 2C is an elevation view of a turbulence inducing heat transfer element within an artery.
Figure 2B:
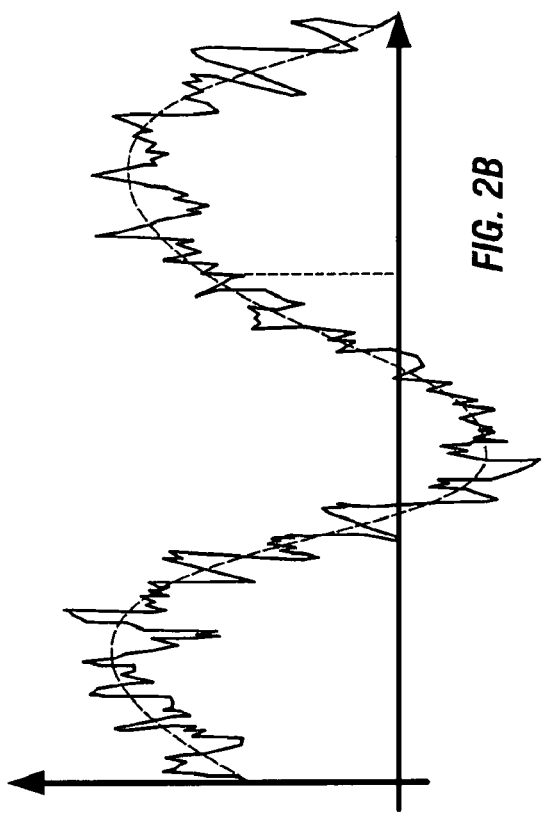
FIG. 2B is a graph illustrating the velocity of steady state turbulent flow under pulsatile conditions as a function of time, similar to arterial blood flow.

FIG. 2C is a perspective view of such a turbulence inducing or mixing-inducing heat transfer element within an artery. In this embodiment, turbulence or mixing is further enhanced by periodically forcing abrupt changes in the direction of the helical blood flow. Turbulent or mixed flow would be found at point 114, in the free stream area. The abrupt changes in flow direction are achieved through the use of a series of two or more heat transfer segments, each comprised of one or more helical ridges. Ideally, the segments will be close enough together to prevent re-laminarization of the flow in between segments.

The use of periodic abrupt changes in the helical direction of the blood flow in order to induce strong free stream turbulence or mixing may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent mixing motion within the clothes-water slurry.

FIG. 4 is an elevation view of one embodiment of a heat transfer element 14 according to the present invention. The heat transfer element 14 is comprised of a series of elongated, articulated segments or modules 20, 22, 24. Three such segments are shown in this embodiment, but two or more such segments could be used without departing from the spirit of the invention. As seen in FIG. 4, a first elongated heat transfer segment 20 is located at the proximal end of the heat transfer element 14. A turbulence-inducing or mixing-inducing exterior surface of the segment 20 comprises four parallel helical ridges 28 with four parallel helical grooves 26 therebetween. One, two, three, or more parallel helical ridges 28 could also be used without departing from the spirit of the present invention. In this embodiment, the helical ridges 28 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first flexible section such as a bellows section 25, which provides flexibility and compressibility. Alternatively, the flexible section may be a simple flexible tube, very similar to a smooth heat transfer segment as shown in FIG. 3C, but flexible. The second heat transfer segment 22 comprises one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second flexible section such as a bellows section 27 or a flexible tube. The third heat transfer segment 24 comprises one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 28, 32, 36 also allow the heat transfer element 14 to maintain a relatively atraumatic profile, thereby minimizing the possibility of damage to the blood vessel wall. A heat transfer element according to the present invention may be comprised of two, three, or more heat transfer segments.

The bellows sections 25, 27 are formed from seamless and nonporous materials, such as metal, and therefore are impermeable to gas, which can be particularly important, depending on the type of working fluid which is cycled through the heat transfer element 14. The structure of the bellows sections 25, 27 allows them to bend, extend and compress, which increases the flexibility of the heat transfer element 14 so that it is more readily able to navigate through blood vessels. The bellows sections 25, 27 also provide for axial compression of the heat transfer element 14, which can limit the trauma when the distal end of the heat transfer element 14 abuts a blood vessel wall. The bellows sections 25, 27 are also able to tolerate cryogenic temperatures without a loss of performance, facilitating use of the heat transfer element in low temperature ablation of tissue.

As an alternative to a heat transfer element 14 made entirely of a metal or a metal-doped polymer, the exterior surfaces of the heat transfer element 14 can be made from metal, and this metal may comprise very high thermal conductivity materials such as nickel, thereby facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities, which is an important feature in a disposable medical device.

Because the heat transfer element 14 may dwell within the blood vessel for extended periods of time, such as 24-48 hours or even longer, it may be desirable to treat the surfaces of the heat transfer element 14 to avoid clot formation. In particular, one may wish to treat the bellows sections 25, 27 because stagnation of the blood flow may occur in the convolutions, thus allowing clots to form and cling to the surface to form a thrombus. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and, thus prevent adherence of clotting factors to the surface.

FIG. 5 is a longitudinal sectional view of the heat transfer element 14 of an embodiment of the invention, taken along line 5-5 in FIG. 4. Some interior contours are omitted for purposes of clarity. An inner tube 42 creates an inner coaxial lumen 42 and an outer coaxial lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner coaxial lumen 40. At the distal end of the heat transfer element 14, the working fluid exits the inner coaxial lumen 40 and enters the outer lumen 46. As the working fluid flows through the outer lumen 46, heat is transferred from the working fluid to the exterior surface 37 of the heat transfer element 14. Because the heat transfer element 14 is constructed from a high conductivity material, the temperature of its exterior surface 37 may reach very close to the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or some other polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid which remains a liquid as the coolant. Other coolants such as freon undergo nucleate boiling and create turbulence through a different mechanism. Saline is a safe coolant because it is non-toxic, and leakage of saline does not result in a gas embolism, which could occur with the use of boiling refrigerants. Since turbulence or mixing in the coolant is enhanced by the shape of the interior surface 38 of the heat transfer element 14, the coolant can be delivered to the heat transfer element 14 at a warmer temperature and still achieve the necessary heat transfer rate. Further, as the working fluid passes through a bellows section into a heat transfer segment, the bellows can create a "jet effect" into the adjacent heat transfer segment, thereby enhancing interior mixing.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at lower flow rates and lower pressures. High pressures may make the heat transfer element stiff and cause it to push against the wall of the blood vessel, thereby shielding part of the exterior surface 37 of the heat transfer element 14 from the blood. Because of the increased heat transfer characteristics achieved by the alternating helical ridges 28, 32, 36, the pressure of the working fluid may be as low as 5 atmospheres, 3 atmospheres, 2 atmospheres or even less than 1 atmosphere.

Figure 6:
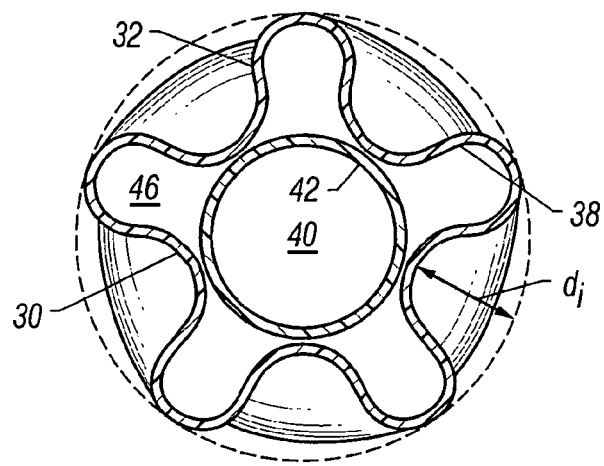
FIG. 6 is a transverse section view of the heat transfer element of FIG. 4.

FIG. 6 is a transverse sectional view of the heat transfer element 14 of the invention, taken at a location denoted by the line 6-6 in FIG. 4. FIG. 6 illustrates a five lobed embodiment, whereas FIG. 4 illustrates a four-lobed embodiment. As mentioned earlier, any number of lobes might be used. In FIG. 6, the coaxial construction of the heat transfer element 14 is clearly shown. The inner coaxial lumen 40 is defined by the insulating coaxial tube 42. The outer lumen 46 is defined by the exterior surface of the insulating coaxial tube 42 and the interior surface 38 of the heat transfer element 14. In addition, the helical ridges 32 and helical grooves 30 may be seen in FIG. 6. If desired, the depth of the grooves, d, can be greater than the boundary layer thickness which would have developed if a cylindrical heat transfer element were introduced. For example, in a heat transfer element 14 with a 4 mm outer diameter, the depth of the invaginations, d, may be approximately equal to 1 mm if designed for use in the carotid artery. Although FIG. 6 shows four ridges and four grooves, the number of ridges and grooves may vary. Thus, heat transfer elements with 1, 2, 3, 4, 5, 6, 7, 8 or more ridges are specifically contemplated.

Figure 7:
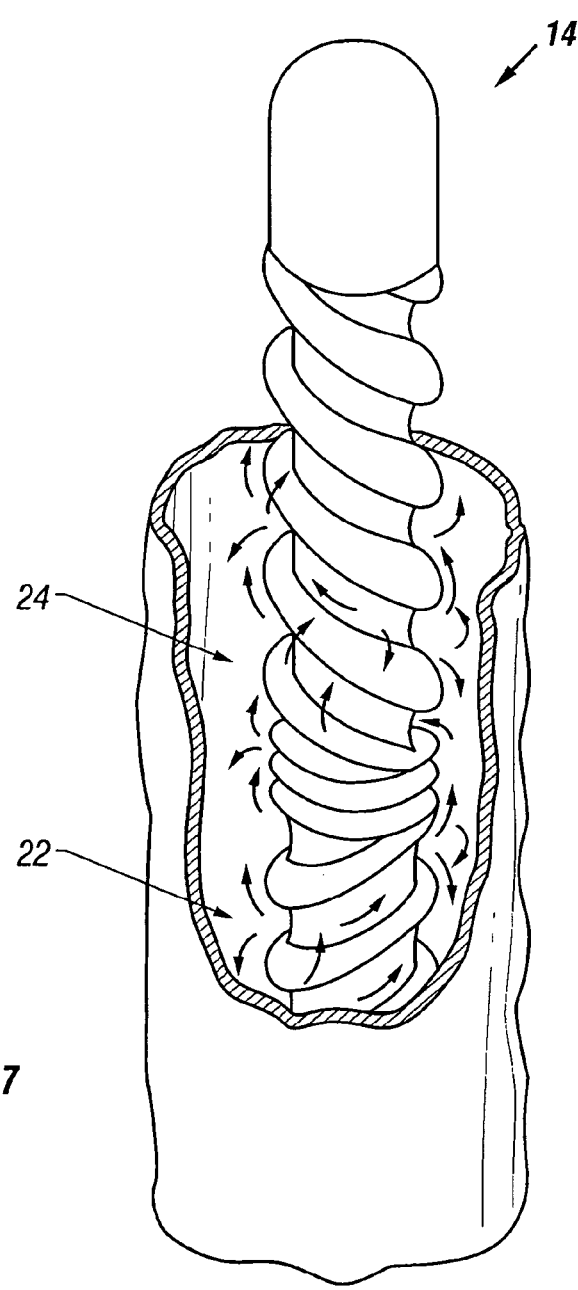
FIG. 7 is a perspective view of the heat transfer element of FIG. 4 in use within a blood vessel.

FIG. 7 is a perspective view of a heat transfer element 14 in use within a blood vessel, showing only one helical lobe per segment for purposes of clarity. Beginning from the proximal end of the heat transfer element (not shown in FIG. 7), as the blood moves forward during the systolic pulse, the first helical heat transfer segment 20 induces a counter-clockwise rotational inertia to the blood. As the blood reaches the second segment 22, the rotational direction of the inertia is reversed, causing turbulence or mixing within the blood. Further, as the blood reaches the third segment 24, the rotational direction of the inertia is again reversed. The sudden changes in flow direction actively reorient and randomize the velocity vectors, thus ensuring turbulence or mixing throughout the bloodstream. During turbulent or mixed flow, the velocity vectors of the blood become more random and, in some cases, become perpendicular to the axis of the artery. In addition, as the velocity of the blood within the artery decreases and reverses direction during the cardiac cycle, additional turbulence or mixing is induced and turbulent motion is sustained throughout the duration of each pulse through the same mechanisms described above.

Thus, a large portion of the volume of warm blood in the vessel is actively brought in contact with the heat transfer element 14, where it can be cooled by direct contact rather than being cooled largely by conduction through adjacent laminar layers of blood. In this embodiment, free stream turbulence or mixing is induced. Where a smooth heat transfer element is not sufficient, in order to create the desired level of turbulence or mixing in the entire blood stream during the whole cardiac cycle, the heat transfer element 14 creates a turbulence intensity greater than about 0.05. The turbulence intensity may be greater than 0.05, 0.06, 0.07 or up to 0.10 or 0.20 or greater.

Referring back to FIG. 4, the heat transfer element 14 has been designed to address all of the design criteria discussed above. First, the heat transfer element 14 is flexible and is made of a highly conductive material. The flexibility is provided by a segmental distribution of flexible sections such as bellows sections 25, 27 or flexible tubes, which provide an articulating mechanism. Bellows have a known convoluted design which provides flexibility. Second, the exterior surface area 37 has been increased through the use of helical ridges 28, 32, 36 and helical grooves 26, 30, 34. The ridges also allow the heat transfer element 14 to maintain a relatively atraumatic profile, thereby minimizing the possibility of damage to the vessel wall. Third, the heat transfer element 14 has been designed to promote turbulent kinetic energy both internally and externally. The modular or segmental design allows the direction of the invaginations to be reversed between segments. The alternating helical rotations create an alternating flow that results in mixing the blood in a manner analogous to the mixing action created by the rotor of a washing machine that switches directions back and forth. This mixing action is intended to promote high level turbulent kinetic energy to enhance the heat transfer rate. The alternating helical design also causes beneficial mixing, or turbulent kinetic energy, of the working fluid flowing internally.

Figure 8:
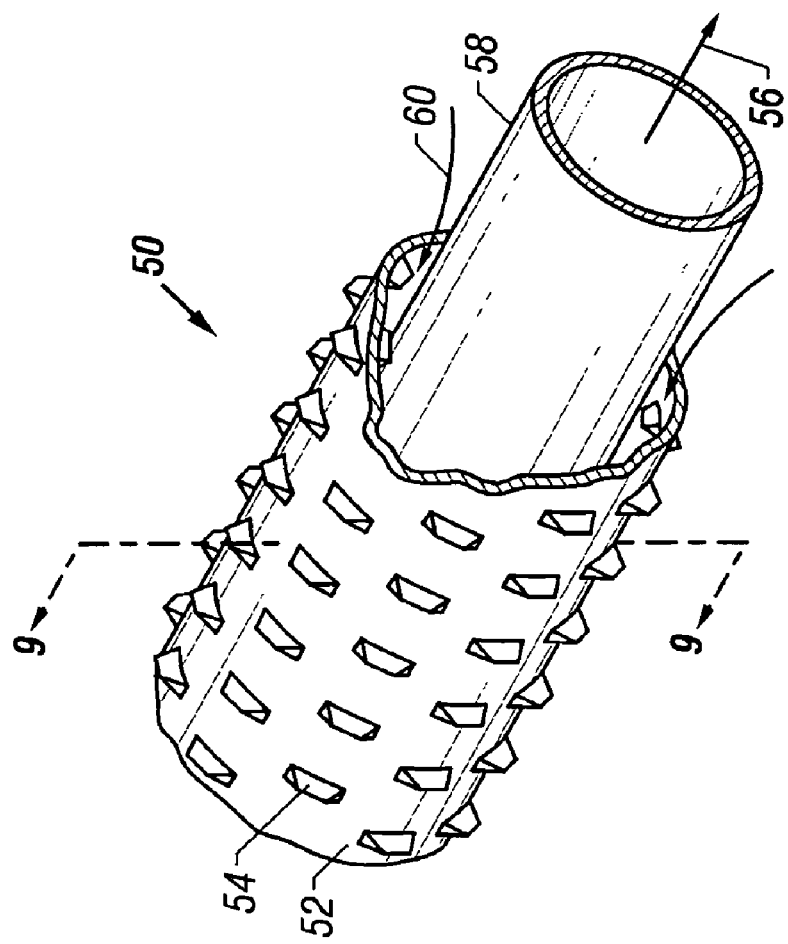
FIG. 8 is a cut-away perspective view of a second embodiment of a heat transfer element according to the invention, with protrusions on the surface.

FIG. 8 is a cut-away perspective view of a second embodiment of a heat transfer element 50. An external surface 52 of the heat transfer element 50 is covered with a series of axially staggered protrusions 54. The staggered nature of the outer protrusions 54 is readily seen with reference to FIG. 9 which is a transverse cross-sectional view taken at a location denoted by the line 9-9 in FIG. 8. If desired, the height, $d_p$, of the staggered outer protrusions 54 can be greater than the thickness of the boundary layer which would develop if a smooth heat transfer element had been introduced into the blood stream. As the blood flows along the external surface 52, it collides with one of the staggered protrusions 54 and a turbulent wake flow is created behind the protrusion. As the blood divides and swirls along side of the first staggered protrusion 54, its turbulent wake encounters another staggered protrusion 54 within its path preventing the re-lamination of the flow and creating yet more turbulence. In this way, the velocity vectors are randomized and turbulence or mixing is created not only in the boundary layer but throughout the free stream. As is the case with the preferred embodiment, this geometry also induces a turbulent or mixing effect on the internal coolant flow.

A working fluid is circulated up through an inner coaxial lumen 56 defined by an insulating coaxial tube 58 to a distal tip of the heat transfer element 50. The working fluid then traverses an outer coaxial lumen 60 in order to transfer heat to the exterior surface 52 of the heat transfer element 50. The inside surface of the heat transfer element 50 is similar to the exterior surface 52, in order to induce turbulent or mixing flow of the working fluid. The inner protrusions can be aligned with the outer protrusions 54, as shown in FIG. 9, or they can be offset from the outer protrusions 54, as shown in FIG. 8.

Figure 9:
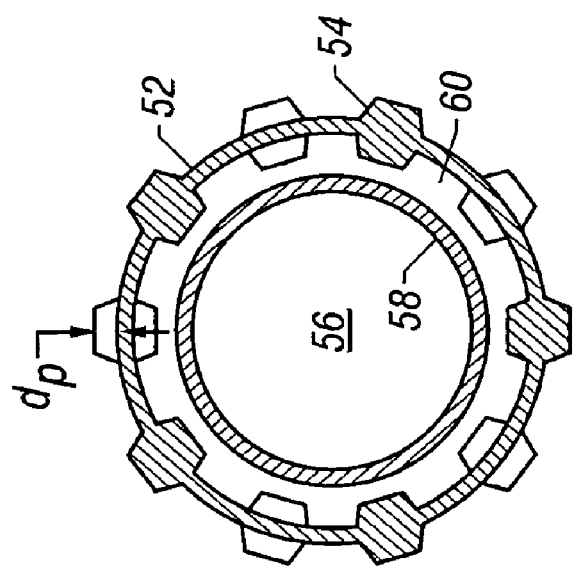
FIG. 9 is a transverse section view of the heat transfer element of FIG. 8.

The embodiment of FIGS. 8 and 9 may result in a Nusselt number ("Nu") of about 1 to 50. The Nusselt number is the ratio of the heat transfer rate with fluid flow to the heat transfer rate in the absence of fluid flow $Nu=Q_{flow}/Q_{no-flow}$. The magnitude of the enhancement in heat transfer by fluid flow can be estimated by the Nusselt number. For convective heat transfer between blood and the surface of the heat transfer element, Nusselt numbers of 30 to 80 have been found to be appropriate for selective cooling applications of various organs in the human body. Nusselt numbers are generally dependent on several other numbers: the Reynolds number, the Womersley number, and the Prandtl number. Enhancement of the heat transfer rate in embodiments of the present invention may be described by a Nusselt number of between 10 and 50.

Figure 10:
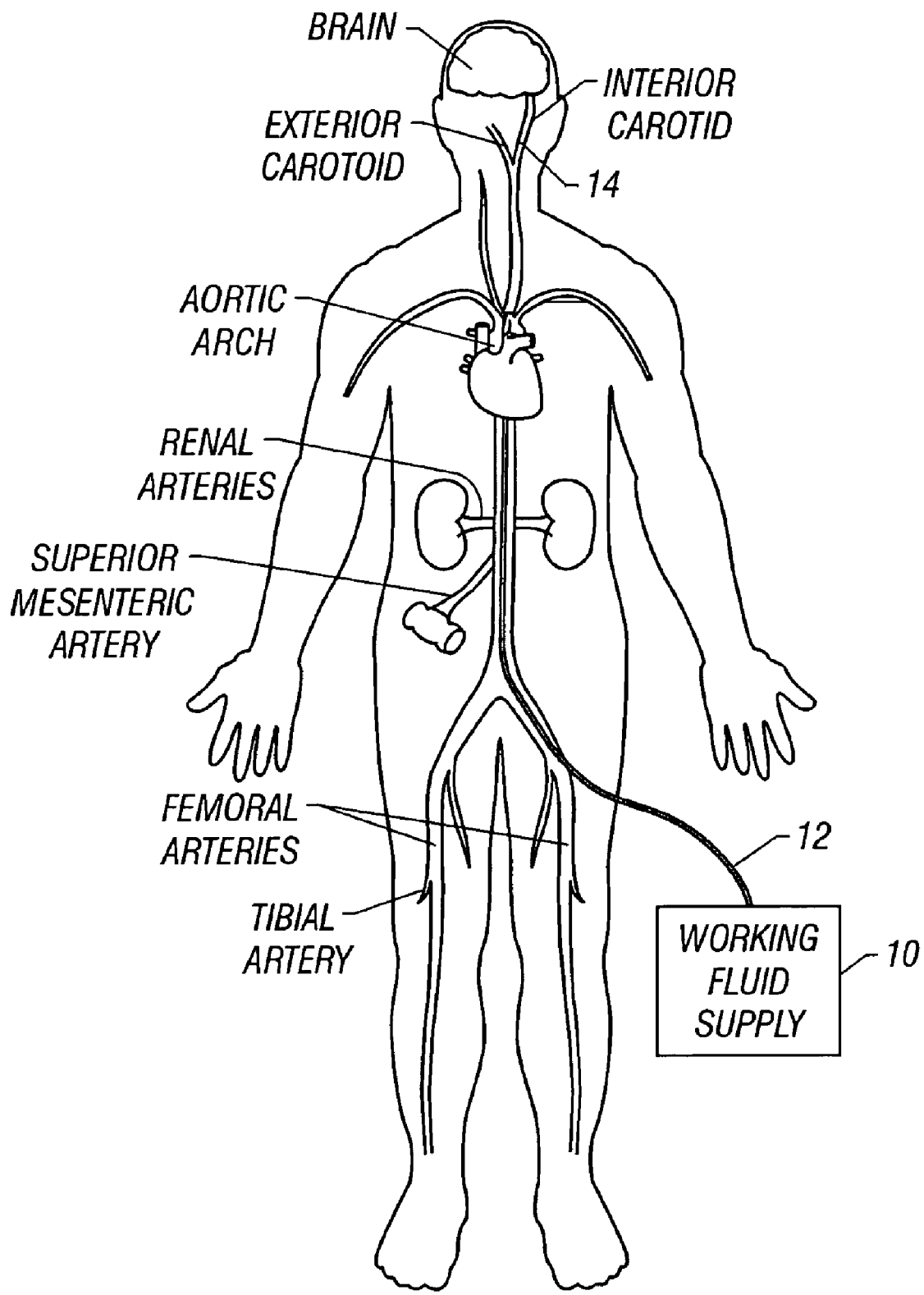
FIG. 10 is a schematic representation of the invention being used in one embodiment to cool the brain of a patient.

FIG. 10 is a schematic representation of the invention being used to cool the brain of a patient. The selective organ hypothermia apparatus shown in FIG. 10 includes a working fluid supply 10, preferably supplying a chilled liquid such as water, alcohol or a halogenated hydrocarbon, a supply catheter 12 and the heat transfer element 14. The supply catheter 12 has a coaxial construction. An inner coaxial lumen within the supply catheter 12 receives coolant from the working fluid supply 10. The coolant travels the length of the supply catheter 12 to the heat transfer element 14 which serves as the cooling tip of the catheter. At the distal end of the heat transfer element 14, the coolant exits the insulated interior lumen and traverses the length of the heat transfer element 14 in order to decrease the temperature of the heat transfer element 14. The coolant then traverses an outer lumen of the supply catheter 12 so that it may be disposed of or recirculated. The supply catheter 12 is a flexible catheter having a diameter sufficiently small to allow its distal end to be inserted percutaneously into an accessible artery such as the femoral artery of a patient as shown in FIG. 10. The supply catheter 12 is sufficiently long to allow the heat transfer element 14 at the distal end of the supply catheter 12 to be passed through the vascular system of the patient and placed in the internal carotid artery or other small artery. The method of inserting the catheter into the patient and routing the heat transfer element 14 into a selected artery is well known in the art.

The working fluid supply 10 would preferably include a chiller and a pump. The pump can be a gear pump, a peristaltic pump, or some other type. A gear pump may be preferable, since the attainable pressure with a gear pump may be higher, and the relationship of the volume flow rate to the pump speed may be more linear with a gear pump than with other pumps. Two types of gear pumps which would be suitable, among others, are radial spur gear pumps and helical tooth gear pumps. A helical tooth gear pump may provide higher pressure and more constant flow rate than a spur gear pump. The ability to achieve high pressures may be important, as the cooling fluid is required to pass through a fairly narrow catheter at a certain, dependable, rate. For the same reason, the viscosity of the fluid, at low temperatures, should be appropriately low.

Although the working fluid supply 10 is shown as an exemplary cooling device, other devices and working fluids may be used. For example, in order to provide cooling, freon, perfluorocarbon, water, or saline may be used, as well as other such coolants.

The heat transfer element can absorb or provide over 75 Watts of heat to the blood stream and may absorb or provide as much as 100 Watts, 150 Watts, 170 Watts or more. For example, a heat transfer element with a diameter of 4 mm and a length of approximately 10 cm using ordinary saline solution chilled so that the surface temperature of the heat transfer element is approximately 5° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer.

Figure 11:
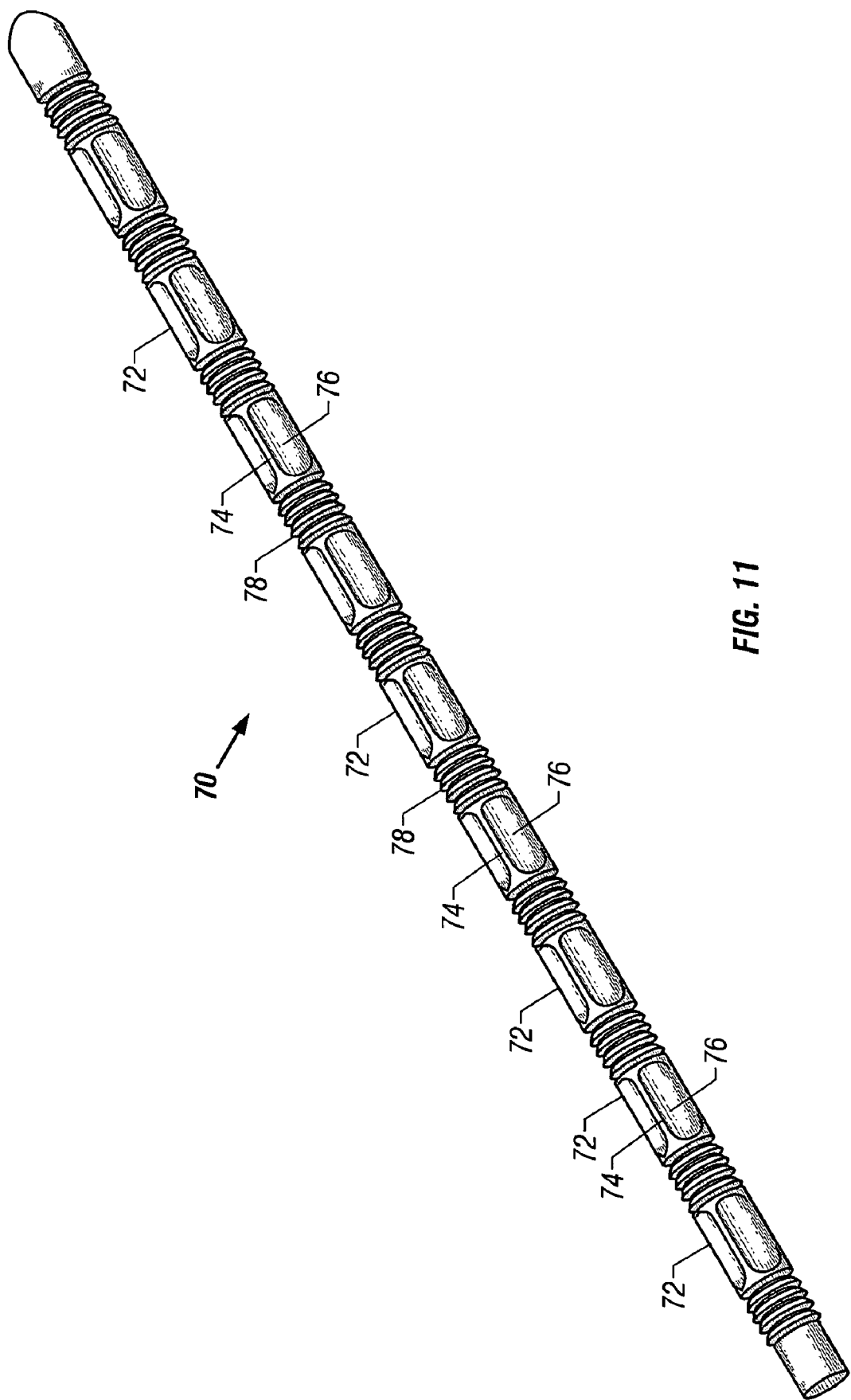
FIG. 11 is a perspective view of a third embodiment of a heat transfer element according to the invention, with aligned longitudinal ridges on adjacent segments.

FIG. 11 is a perspective view of a third embodiment of a heat transfer element 70 according to the present invention. The heat transfer element 70 is comprised of a series of elongated, articulated segments or modules 72. A first elongated heat transfer segment 72 is located at the proximal end of the heat transfer element 70. The segment 72 may be a smooth right circular cylinder, as addressed in FIG. 3C, or it can incorporate a turbulence-inducing or mixing-inducing exterior surface. The turbulence-inducing or mixing-inducing exterior surface shown on the segment 72 in FIG. 11 comprises a plurality of parallel longitudinal ridges 74 with parallel longitudinal grooves 76 therebetween. One, two, three, or more parallel longitudinal ridges 74 could be used without departing from the spirit of the present invention. In the embodiment where they are used, the longitudinal ridges 74 and the longitudinal grooves 76 of the heat transfer segment 72 are aligned parallel with the axis of the first heat transfer segment 72.

The first heat transfer segment 72 is coupled to a second elongated heat transfer segment 72 by a first flexible section such as a bellows section 78, which provides flexibility and compressibility. Alternatively, the flexible section may be a simple flexible tube, very similar to a smooth heat transfer segment as addressed in FIG. 3C, but flexible. The second heat transfer segment 72 also comprises a plurality of parallel longitudinal ridges 74 with parallel longitudinal grooves 76 therebetween. The longitudinal ridges 74 and the longitudinal grooves 76 of the second heat transfer segment 72 are aligned parallel with the axis of the second heat transfer segment 72. The second heat transfer segment 72 is coupled to a third elongated heat transfer segment 72 by a second flexible section such as a bellows section 78 or a flexible tube. The third heat transfer segment 72 also comprises a plurality of parallel longitudinal ridges 74 with parallel longitudinal grooves 76 therebetween. The longitudinal ridges 74 and the longitudinal grooves 76 of the third heat transfer segment 72 are aligned parallel with the axis of the third heat transfer segment 72. Further, in this embodiment, adjacent heat transfer segments 72 of the heat transfer element 70 have their longitudinal ridges 74 aligned with each other, and their longitudinal grooves 76 aligned with each other.

In addition, the rounded contours of the ridges 74 also allow the heat transfer element 70 to maintain a relatively atraumatic profile, thereby minimizing the possibility of damage to the blood vessel wall. A heat transfer element 70 according to the present invention may be comprised of two, three, or more heat transfer segments 72.

The bellows sections 78 are formed from seamless and nonporous materials, such as metal, and therefore are impermeable to gas, which can be particularly important, depending on the type of working fluid which is cycled through the heat transfer element 70. The structure of the bellows sections 78 allows them to bend, extend and compress, which increases the flexibility of the heat transfer element 70 so that it is more readily able to navigate through blood vessels. The bellows sections 78 also provide for axial compression of the heat transfer element 70, which can limit the trauma when the distal end of the heat transfer element 70 abuts a blood vessel wall. The bellows sections 78 are also able to tolerate cryogenic temperatures without a loss of performance, facilitating use of the heat transfer element in low temperature ablation of tissue.

FIG. 12 is a perspective view of a fourth embodiment of a heat transfer element 80 according to the present invention. The heat transfer element 80 is comprised of a series of elongated, articulated segments or modules 82. A first elongated heat transfer segment 82 is located at the proximal end of the heat transfer element 80. A turbulence-inducing or mixing-inducing exterior surface of the segment 82 comprises a plurality of parallel longitudinal ridges 84 with parallel longitudinal grooves 86 therebetween. One, two, three, or more parallel longitudinal ridges 84 could be used without departing from the spirit of the present invention. In this embodiment, the longitudinal ridges 84 and the longitudinal grooves 86 of the heat transfer segment 82 are aligned parallel with the axis of the first heat transfer segment 82.

The first heat transfer segment 82 is coupled to a second elongated heat transfer segment 82 by a first flexible section such as a bellows section 88, which provides flexibility and compressibility. Alternatively, the flexible section may be a simple flexible tube, very similar to a smooth heat transfer segment as shown in FIG. 3C, but flexible. The second heat transfer segment 82 also comprises a plurality of parallel longitudinal ridges 84 with parallel longitudinal grooves 86 therebetween. The longitudinal ridges 84 and the longitudinal grooves 86 of the second heat transfer segment 82 are aligned parallel with the axis of the second heat transfer segment 82. The second heat transfer segment 82 is coupled to a third elongated heat transfer segment 82 by a second flexible section such as a bellows section 88 or a flexible tube. The third heat transfer segment 82 also comprises a plurality of parallel longitudinal ridges 84 with parallel longitudinal grooves 86 therebetween. The longitudinal ridges 84 and the longitudinal grooves 86 of the third heat transfer segment 82 are aligned parallel with the axis of the third heat transfer segment 82. Further, in this embodiment, adjacent heat transfer segments 82 of the heat transfer element 80 have their longitudinal ridges 84 angularly offset from each other, and their longitudinal grooves 86 angularly offset from each other. Offsetting of the longitudinal ridges 84 and the longitudinal grooves 86 from each other on adjacent segments 82 promotes turbulence or mixing in blood flowing past the exterior of the heat transfer element 80.

FIG. 13 is a transverse section view of a heat transfer segment 90, illustrative of segments 72, 82 of heat transfer elements 70, 80 shown in FIG. 11 and FIG. 12. The coaxial construction of the heat transfer segment 90 is clearly shown. The inner coaxial lumen 92 is defined by the insulating coaxial tube 93. The outer lumen 98 is defined by the exterior surface of the insulating coaxial tube 93 and the interior surface 99 of the heat transfer segment 90. In addition, parallel longitudinal ridges 94 and parallel longitudinal grooves 96 may be seen in FIG. 13. The longitudinal ridges 94 and the longitudinal grooves 96 may have a relatively rectangular cross-section, as shown in FIG. 13, or they may be more triangular in cross-section, as shown in FIGS. 11 and 12. The longitudinal ridges 94 and the longitudinal grooves 96 may be formed only on the exterior surface of the segment 90, with a cylindrical interior surface 99. Alternatively, corresponding longitudinal ridges and grooves may be formed on the interior surface 99 as shown, to promote turbulence or mixing in the working fluid. Although FIG. 13 shows six ridges and six grooves, the number of ridges and grooves may vary. Where a smooth exterior surface is desired, the outer tube of the heat transfer segment 90 could have smooth outer and inner surfaces, like the inner tube 93. Alternatively, the outer tube of the heat transfer segment 90 could have a smooth outer surface and a ridged inner surface like the interior surface 99 shown in FIG. 13.

The practice of the invention is illustrated in the following non-limiting example.

Exemplary Procedure

1. The patient is initially assessed, resuscitated, and stabilized.
2. The procedure is carried out in an angiography suite or surgical suite equipped with fluoroscopy.
3. Because the catheter is placed into the common carotid artery, it is important to determine the presence of stenotic atheromatous lesions. A carotid duplex (doppler/ultrasound) scan can quickly and non-invasively make this determinations. The ideal location for placement of the catheter is in the left carotid so this may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities >100 cm/sec in the internal indicate the presence of at least 70% stenosis. Stenosis of 70% or more may warrant the placement of a stent to open up the internal artery diameter.
4. The ultrasound can also be used to determine the vessel diameter and the blood flow and the catheter with the appropriately sized heat transfer element could be selected.

5. After assessment of the arteries, the patients inguinal region is sterilely prepped and infiltrated with lidocaine.
6. The femoral artery is cannulated and a guide wire may be inserted to the desired carotid artery. Placement of the guide wire is confirmed with fluoroscopy.
7. An angiographic catheter can be fed over the wire and contrast media injected into the artery to further to assess the anatomy of the carotid.
8. Alternatively, the femoral artery is cannulated and a 10-12.5 french (f) introducer sheath is placed.
9. A guide catheter is placed into the desired common carotid artery. If a guiding catheter is placed, it can be used to deliver contrast media directly to further assess carotid anatomy.
10. A 10 f-12 f (3.3-4.0 mm) (approximate) cooling catheter is subsequently filled with saline and all air bubbles are removed.
11. The cooling catheter is placed into the carotid artery via the guiding catheter or over the guidewire. Placement is confirmed with fluoroscopy.
12. Alternatively, the cooling catheter tip is shaped (angled or curved approximately 45 degrees), and the cooling catheter shaft has sufficient pushability and torqueability to be placed in the carotid without the aid of a guide wire or guide catheter.
13. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
14. Cooling is initiated by starting the pump mechanism. The saline within the cooling catheter is circulated at 5 cc/sec. The saline travels through the heat exchanger in the chilled water bath and is cooled to approximately 1° C.
15. It subsequently enters the cooling catheter where it is delivered to the heat transfer element. The saline is warmed to approximately 5-7° C. as it travels along the inner lumen of the catheter shaft to the end of the heat transfer element.
16. The saline then flows back through the heat transfer element in contact with the inner metallic surface. The saline is further warmed in the heat transfer element to 12-15° C., and in the process, heat is absorbed from the blood, cooling the blood to 30° to 32° C.
17. The chilled blood then goes on to chill the brain. It is estimated that 15-30 minutes will be required to cool the brain to 30 to 32° C.
18. The warmed saline travels back down the outer lumen of the catheter shaft and back to the chilled water bath where it is cooled to 1° C.
19. The pressure drops along the length of the circuit are estimated to be 2-3 atm.
20. The cooling can be adjusted by increasing or decreasing the flow rate of the saline. Monitoring of the temperature drop of the saline along the heat transfer element will allow the flow to be adjusted to maintain the desired cooling effect.
21. The catheter is left in place to provide cooling for 12 to 24 hours.
22. If desired, warm saline can be circulated to promote warming of the brain at the end of the therapeutic cooling period.

The invention herein disclosed is capable of obtaining the stated objects, but no limitations are intended other than as described in the appended claims.

We claim:

1. A heat transfer device for low temperature ablation of tissue, said heat transfer device comprising:
   first and second elongated segments, one of said first or second elongated segments providing a closed end of said heat transfer device;
   a bellows structure connecting said first and second elongated segments, said bellows structure being structured to be less thermally conductive than said first and second elongated segments by virtue of inherent fluid stagnation on the surface of said bellows structure; and
   a tubular conduit disposed within and extending substantially through said first and second elongated segments, said conduit having an inner lumen for transporting a working fluid to a distal end of said one of said first or second elongated segments providing a closed end of said heat transfer device.

2. The device recited in claim 1, further comprising a smooth outer surface on at least one of said first and second elongated segments.

3. The device recited in claim 1, wherein said first and second elongated segments are formed from highly conductive material.

4. The device recited in claim 1, further comprising:
   a coaxial supply catheter having an inner catheter lumen coupled to said inner lumen of said tubular conduit; and
   a working fluid supply configured to dispense said working fluid and having an output coupled to said inner catheter lumen.

5. The device recited in claim 4, wherein said working fluid supply is adapted to dispense a perfluorocarbon working fluid.

6. The device recited in claim 4, wherein said working fluid supply is adapted to produce pressurized working fluid at a temperature less than about 0 degrees C.

7. The device recited in claim 1, further comprising:
   at least one additional elongated segment; and
   at least one additional bellows structure connecting said at least one additional elongated segment to one of said first and second elongated segments.

8. The device recited in claim 1, wherein said bellows structure is less thermally conductive than said first and second elongated segments by virtue of fluid stagnation on an outer surface of said bellows structure.

9. The device recited in claim 1, wherein said bellows structure is less thermally conductive than said first and second elongated segments by virtue of fluid stagnation on an inner surface of said bellows structure.

10. The device recited in claim 1, wherein said bellows structure is less thermally conductive than said first and second elongated segments by virtue of fluid stagnation on both inner and outer surfaces of said bellows structure.

* * * * *